United States Patent [19]

Rottinghaus et al.

[11] Patent Number: 6,076,527

[45] Date of Patent: Jun. 20, 2000

[54] ADAPTIVE PATIENT SUPPORT AND RESTRAINT SYSTEM

[76] Inventors: Herman James Rottinghaus, 1500 Bluebird Cir., Stow, Ohio 44224; Eli Saul Asher, 225 W. Second St., Perrysburg, Ohio 43551; Stephen William Butcher, 3456 Marsh Rd., Stow, Ohio 44224; Anthony Mark Demore, 6 Honeybee Ct., Apartment H, Cockeysville, Md. 21030; Soo Hyun Ham, 500 Group 1 Fancett Pl., Greenwich, Conn. 06830

[21] Appl. No.: 09/004,245

[22] Filed: Jan. 8, 1998

[51] Int. Cl.[7] .................................................. A61B 19/00

[52] U.S. Cl. ........................... 128/869; 128/875; 128/876; 297/484; 297/485

[58] Field of Search .................................... 128/846, 873, 128/874, 875, 876; 297/484, 485

[56] References Cited

U.S. PATENT DOCUMENTS

| D. 275,230 | 8/1984 | Hubbard et al. . |
|---|---|---|
| 1,236,454 | 8/1917 | Lawrence . |
| 1,808,496 | 6/1931 | Dillon . |

(List continued on next page.)

FOREIGN PATENT DOCUMENTS

| 141896 A1 | 5/1985 | European Pat. Off. . |
|---|---|---|
| 525393 A1 | 2/1993 | European Pat. Off. . |
| 636325 A2 | 2/1995 | European Pat. Off. . |
| WO 94/06327 | 3/1994 | WIPO . |
| WO 94/24893 | 11/1994 | WIPO . |
| WO 95/04515 | 2/1995 | WIPO . |
| WO 95/09545 | 4/1995 | WIPO . |

OTHER PUBLICATIONS

Huggin' arms Miracle Baby Sitter, Marketing Sheet.
Uppertone Unassisted Muscle Strengthening System for Quads, Product Literature.
Wheelchair Control System, the PHC–2 from Peachtree Head Control Systems, Product Literature.
Cybex Strength Systems, Product Literature.
Skil–Care, Co., XP002013502, "Products Catalog".
Sammons Catalogue, 1994 Edition, pp. 39, 75, 86, 87, 88, 89, 90, 91, 96, 97, 98, 100, 101, 102, 104, 105, 108, 109, 110, 264, 265, 266, 267, 268.

Primary Examiner—Michael A. Brown
Attorney, Agent, or Firm—Knoble & Yoshida LLC

[57] ABSTRACT

An adaptive patient support and restraint system provides (i) selective delivery of physical support, physical restraint, or physical support and physical restraint to control movement of the patient's upper body and lower body, (ii) adjustable delivery of physical support, physical restraint, or physical support and physical restraint to accommodate a range of patient sizes, various chair, gerichair, wheelchair, and bed sizes and types, (iii) variable delivery of physical support, physical restraint, or physical support and physical restraint to accommodate a range of patient medical and safety needs, and (iv) distributive delivery of physical support, physical restraint, or physical support and physical restraint to distribute stresses associated with support and restraint over a broad area of a patient's body. The adaptive patient support and restraint system includes a belt system, a garment system, and seating cushion system. The belt system can be used as a stand-alone system, in combination with the garment system, in combination with the seating cushion system, or in combination with the garment system and the seating cushion system, to provide the degree of physical control necessary to accommodate the medical and safety requirements of a range of patients. The seating cushion system can be used as a stand-alone system, in combination with the belt system, or in combination with the belt system and the garment system to provide the degree of physical control necessary to accommodate the medical and safety requirements of a range of patients.

39 Claims, 18 Drawing Sheets

U.S. PATENT DOCUMENTS

| | | |
|---|---|---|
| 2,044,390 | 6/1936 | Kiehs . |
| 2,362,465 | 11/1944 | Carner . |
| 2,374,712 | 5/1945 | Steigerwald . |
| 2,459,068 | 1/1949 | Eastwood . |
| 2,745,465 | 5/1956 | Hogan . |
| 2,751,594 | 6/1956 | Brissenden . |
| 2,755,841 | 7/1956 | Reinholz . |
| 2,796,533 | 6/1957 | Morton et al. . |
| 2,827,898 | 3/1958 | Thompson . |
| 2,851,033 | 9/1958 | Posey . |
| 2,857,735 | 10/1958 | Mashl . |
| 3,098,479 | 7/1963 | Storey . |
| 3,100,484 | 8/1963 | Berl . |
| 3,108,292 | 10/1963 | Bodnar et al. . |
| 3,136,311 | 6/1964 | Lewis . |
| 3,137,294 | 6/1964 | Robertson . |
| 3,181,530 | 5/1965 | Storey . |
| 3,182,338 | 5/1965 | Shirrod . |
| 3,191,599 | 6/1965 | Kendell . |
| 3,236,234 | 2/1966 | Buckley . |
| 3,265,065 | 8/1966 | Jillson . |
| 3,276,431 | 10/1966 | Murcott . |
| 3,339,209 | 9/1967 | Larson . |
| 3,488,088 | 1/1970 | Goldberg et al. . |
| 3,536,357 | 10/1970 | Murcott . |
| 3,604,750 | 9/1971 | Doering . |
| 3,641,997 | 2/1972 | Posey, Jr. . |
| 3,669,107 | 6/1972 | Posey . |
| 3,742,945 | 7/1973 | Reinhardt . |
| 3,778,052 | 12/1973 | Andow et al. . |
| 3,788,309 | 1/1974 | Zeilman . |
| 3,901,229 | 8/1975 | Hensel et al. . |
| 4,026,282 | 5/1977 | Thomas . |
| 4,073,537 | 2/1978 | Hammersburg . |
| 4,108,170 | 8/1978 | Spann . |
| 4,117,840 | 10/1978 | Rasure . |
| 4,132,230 | 1/1979 | Ladd . |
| 4,170,991 | 10/1979 | Kella . |
| 4,177,807 | 12/1979 | Ocel et al. . |
| 4,330,152 | 5/1982 | Legan et al. . |
| 4,360,014 | 11/1982 | Manahan . |
| 4,402,502 | 9/1983 | Peters . |
| 4,478,213 | 10/1984 | Redding . |
| 4,488,544 | 12/1984 | Triunfol . |
| 4,509,797 | 4/1985 | Mullaly . |
| 4,536,903 | 8/1985 | Parker . |
| 4,541,425 | 9/1985 | Yetter, Jr. . |
| 4,570,268 | 2/1986 | Freeman . |
| 4,571,000 | 2/1986 | Holder . |
| 4,579,390 | 4/1986 | Guille . |
| 4,593,929 | 6/1986 | Williams . |
| 4,615,335 | 10/1986 | Searcy . |
| 4,621,804 | 11/1986 | Mueller . |
| 4,676,554 | 6/1987 | Harlick et al. . |
| 4,685,454 | 8/1987 | Posey . |
| 4,707,031 | 11/1987 | Meistrell . |
| 4,744,354 | 5/1988 | Triunfol . |
| 4,795,176 | 1/1989 | Harrigan et al. . |
| 4,807,937 | 2/1989 | Harrigan . |
| 4,827,920 | 5/1989 | Rowell, Sr. . |
| 4,832,053 | 5/1989 | McCarthy . |
| 4,840,189 | 6/1989 | Wachtel . |
| 4,898,425 | 2/1990 | Mundy . |
| 4,941,497 | 7/1990 | Prather et al. . |
| 4,947,869 | 8/1990 | Grant . |
| 4,971,073 | 11/1990 | Schneider . |
| 4,979,779 | 12/1990 | Williams . |
| 4,981,307 | 1/1991 | Walsh . |
| 4,989,836 | 2/1991 | Hudson, III et al. . |
| 5,042,878 | 8/1991 | Collins . |
| 5,056,533 | 10/1991 | Solano . |
| 5,058,912 | 10/1991 | Harroun . |
| 5,076,264 | 12/1991 | Lonardo et al. . |
| 5,148,563 | 9/1992 | Klearman et al. . |
| 5,154,487 | 10/1992 | Warburton . |
| 5,241,708 | 9/1993 | Rodarmel . |
| 5,256,135 | 10/1993 | Avihod . |
| 5,267,352 | 12/1993 | Rodarmel . |
| 5,271,422 | 12/1993 | Sorrell et al. . |
| 5,284,131 | 2/1994 | Gray . |
| 5,297,852 | 3/1994 | Morales-Quintero . |
| 5,333,623 | 8/1994 | Fuller . |
| 5,351,700 | 10/1994 | Jones, III et al. . |
| 5,366,277 | 11/1994 | Tremblay . |
| 5,395,158 | 3/1995 | Cordia . |
| 5,397,171 | 3/1995 | Leach . |
| 5,400,803 | 3/1995 | Vines . |
| 5,407,248 | 4/1995 | Jay et al. . |
| 5,502,851 | 4/1996 | Costello . |
| 5,511,854 | 4/1996 | Cordia . |
| 5,522,404 | 6/1996 | Williams . |
| 5,540,239 | 7/1996 | McClellan . |

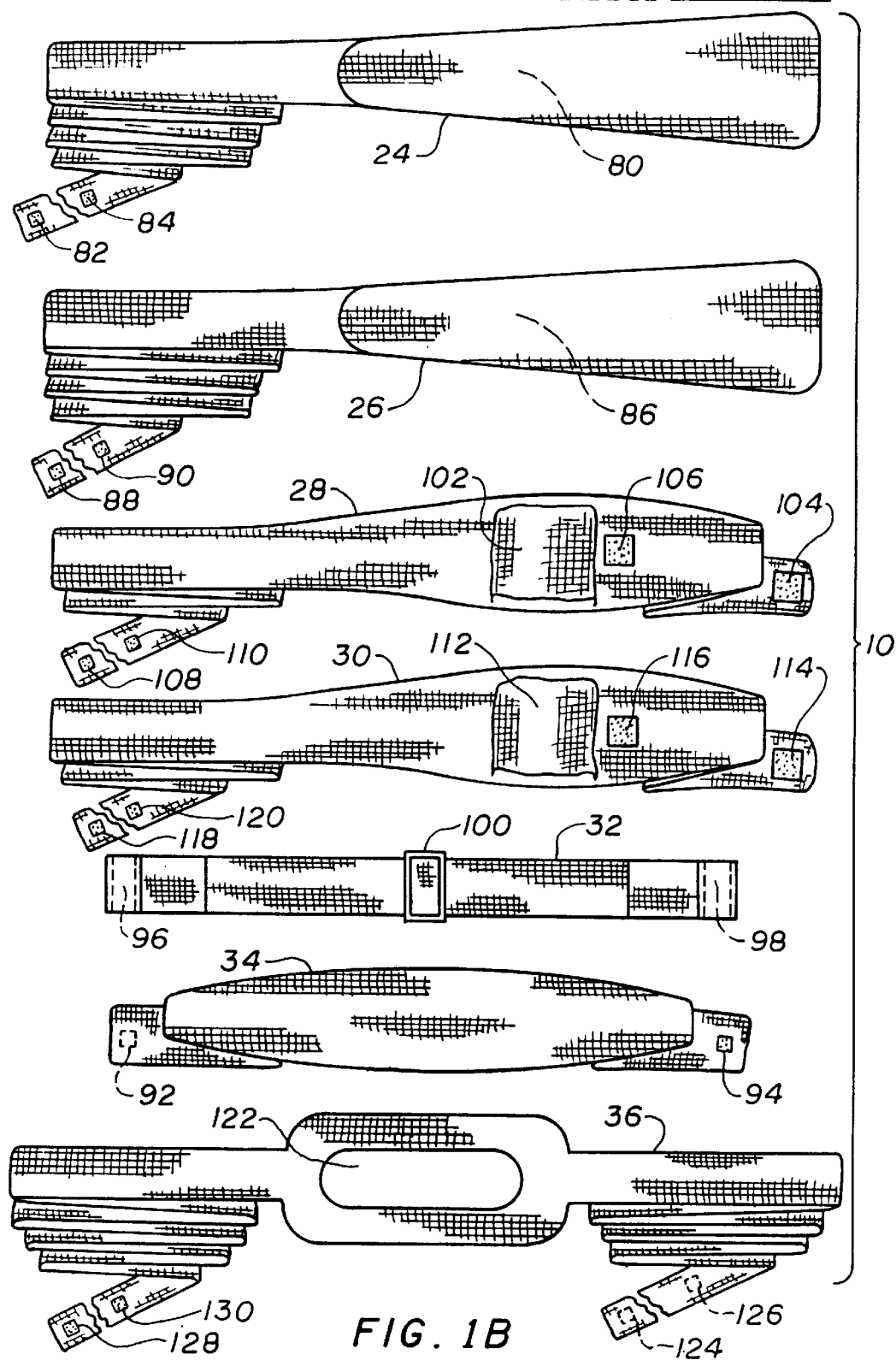

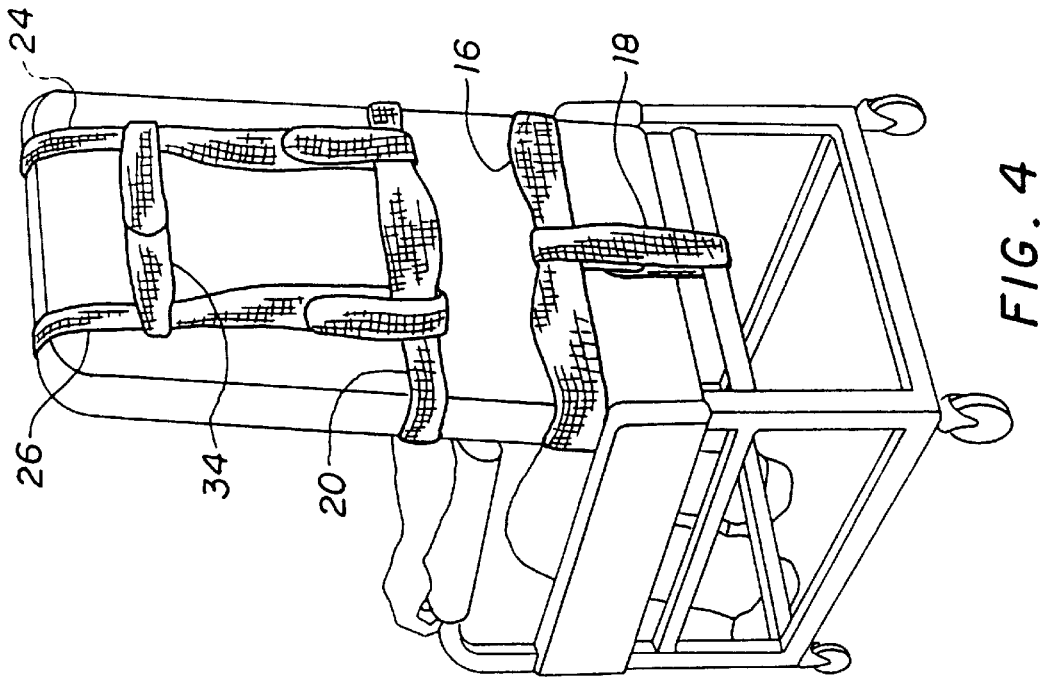
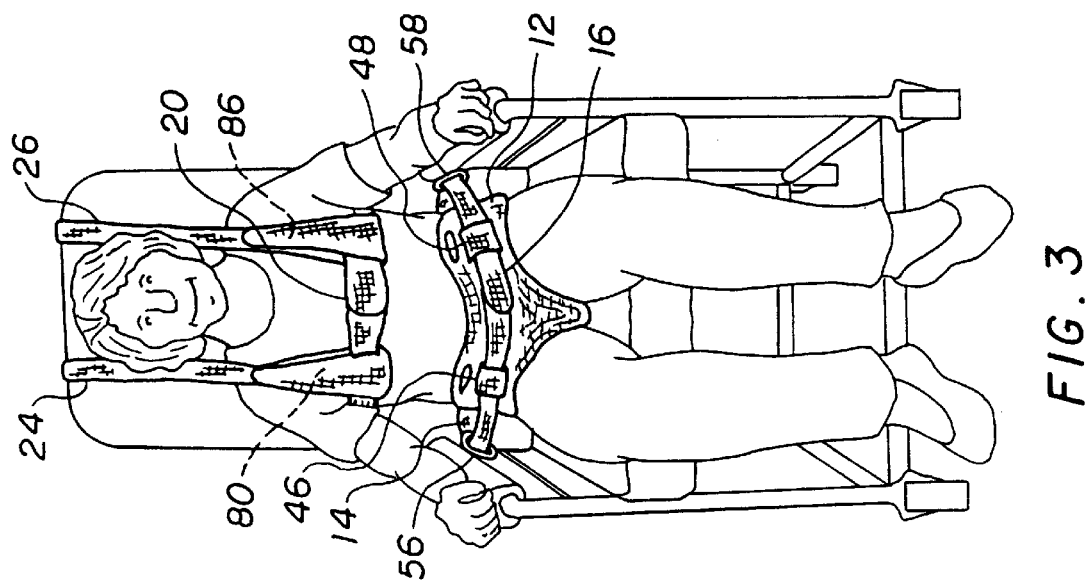

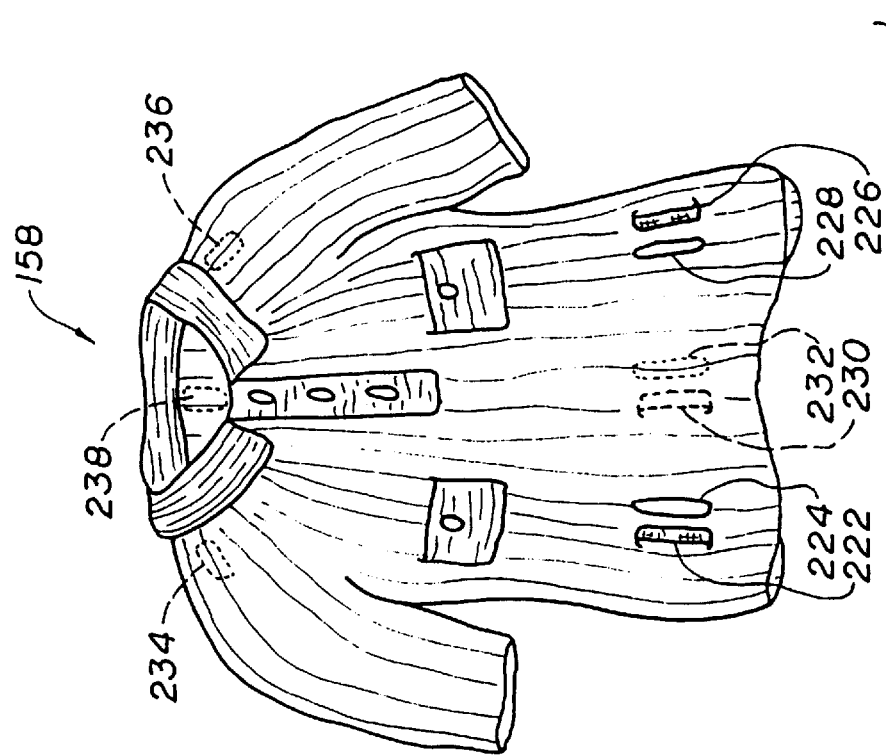
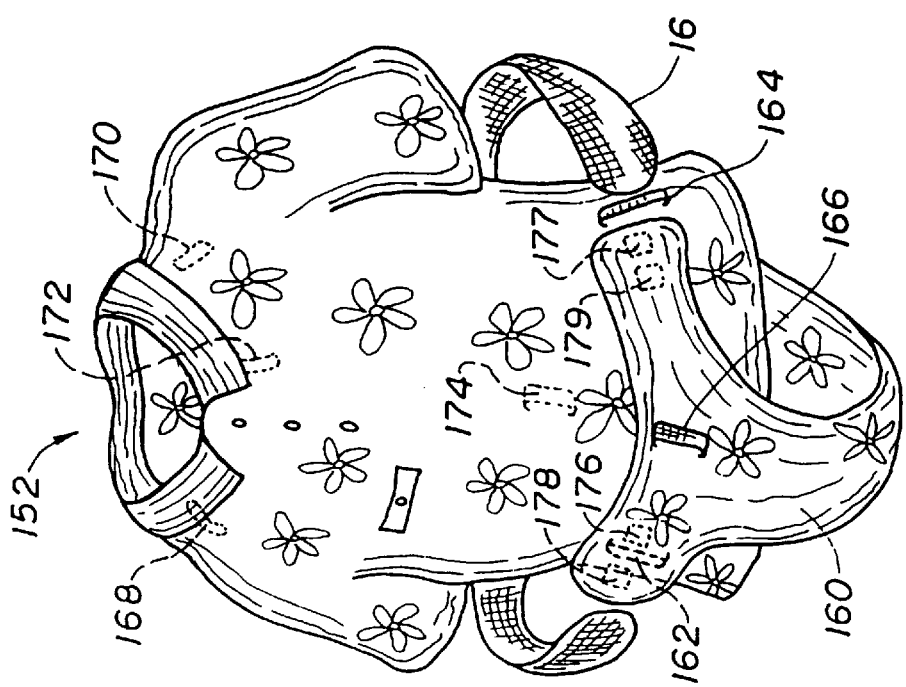
FIG. IIA
MATCH TO FIG. IIB

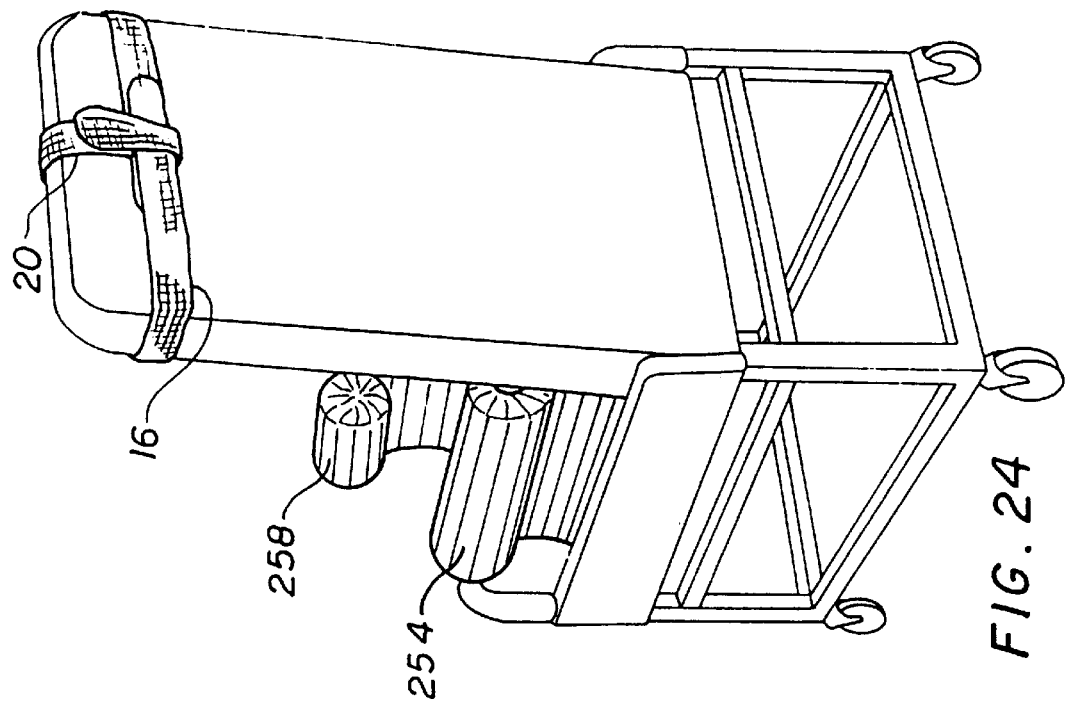
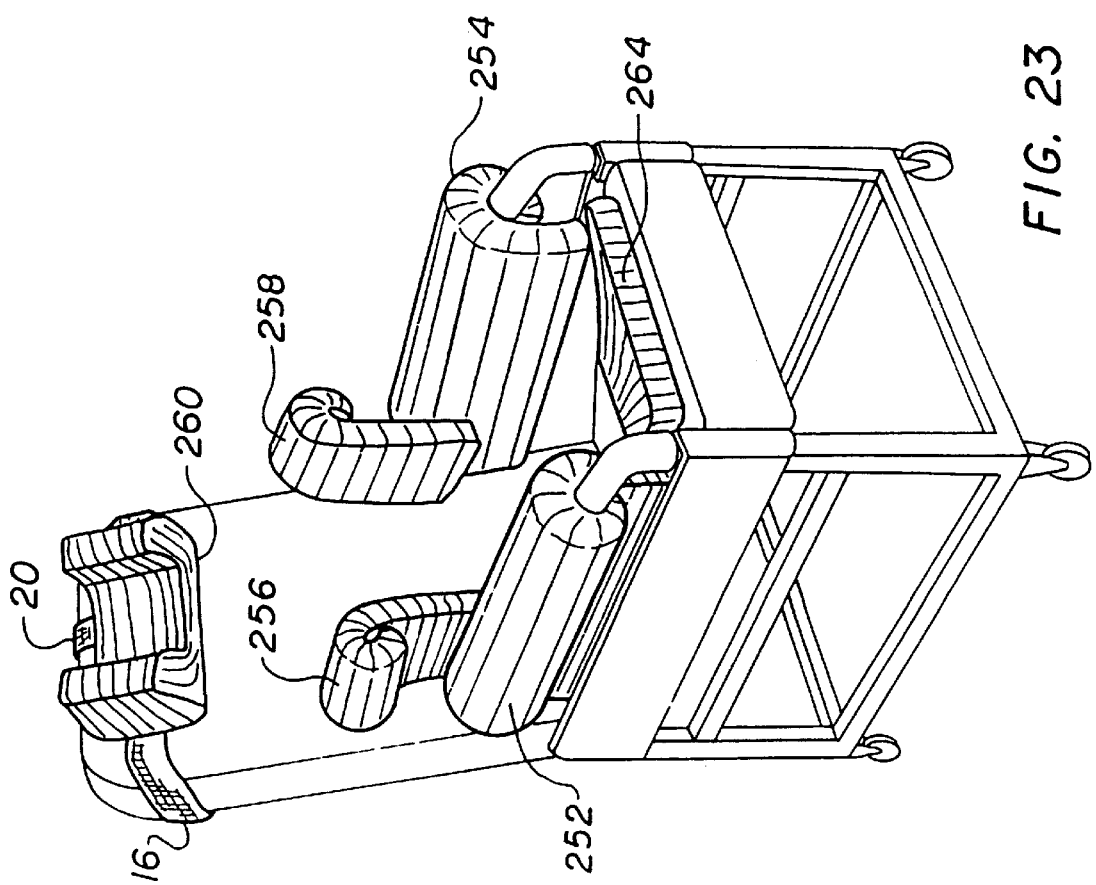

ADAPTIVE PATIENT SUPPORT AND RESTRAINT SYSTEM

FIELD OF THE INVENTION

The present invention relates generally to patient support and restraint systems, and, more specifically, to a belt system, a garment system, and a seating cushion system for providing adaptive patient support and restraint.

BACKGROUND OF THE INVENTION

Many individuals, particularly the elderly, experience physical, mental or emotional disabilities which require some form of physical assistance. However, current patient assistance systems do not permit caregivers to care for patients in a humane way so as to facilitate maintaining each patient's self-dignity while at the same time providing the level of support or restraint necessary to accommodate each patient's medical and safety needs. An important element in delivering care to these individuals is to provide safe and comfortable ergonomic interface with their local environment to allow these individuals to maintain their dignity and to be free of restraint which is not medically necessary.

Many patients are frail and cannot sit up properly without some type of support. For example, a patient seated in a chair, a gerichair, or a wheelchair frequently slouches, slumps, slides down, leans to one side, or leans forward at the waist, therefore requiring some type of posture support or restraint which prevents the aforementioned problems and which also comfortably prevents the patient from falling out of the chair.

Patients are placed in physical restraints for various reasons. For example, patients afflicted with dementia or Alzheimer's disease may be physically restrained to be prevented from wandering; patients exhibiting antisocial behavior or having the potential for violence may be physically restrained to be prevented from inflicting injury upon either themselves or others; and patients lacking the strength to stand or walk, or having the potential for falling, may be physically restrained. However, many patients may be unnecessarily physically restrained in situations where a support device could be used to satisfy both medical and safety requirements.

Several physical control needs of nonambulatory patients and frail patients, particularly in the area of support are going unmet in nursing homes, long term care facilities, assisted living environments and private homes. For example, many such patients encounter difficulties in supporting themselves in gerichairs, wheelchairs, or other settings, and require physical support to avoid falling, leaning side to side, falling forward, slouching, slumping or sliding. Further, many frail patients or Alzheimer's patients require physical restraint while sitting in a chair or while laying in bed to prevent them from injuring themselves. Current support systems are functionally limited, application specific systems that are not easily configurable or adaptable to enable patients of various sizes, using various chair sizes and types, to be adequately supported. In effect, current restraint systems are functionally limited, application specific systems that are difficult for the caregiver to use and uncomfortable for the patient to wear. In addition, these systems can cause damage to the patient's skin such as cutting, chafing, or irritating and thus cause a new medical problem requiring treatment.

The physical support or restraining needs of individual patients frequently change with improvements or deteriorations in the patient's health status. For example, one patient might require minimal physical support, another patient might require moderate physical support, and still another patient might require physical restraint. Current devices are single purpose devices or are part of a series of single purpose devices which provide only a limited range or level of patient support or a limited range or level of patient restraint. A need exists for a cost effective patient assistance system that permits the caregiver to interchange the configuration of the elements of a patient assistance system so that a single system can be used for the purpose of providing physical support as well as physical restraint as the patient's needs and condition change.

In nursing homes and in other medical care settings, clothing worn by patients functions for a single purpose: as a garment for covering the patient's body. Specially designed stretchable garments, however, can be used as a means to enhance support or restraint for a patient if they are utilized in combination with a flexible belt support or belt restraint system. Such a system would spread the stress of support or restraint over a patient's entire body rather than focus the stress on one body area and also allow the patient more natural freedom of movement. The garment system would also provide physical support or physical restraint in an unobtrusive manner, thus allowing patients to preserve their self dignity. A need exists for a multi-purpose garment system that functions in combination with a flexible patient support and restraint system to physically control the movement of the patient's body, while also functioning as a stylish wardrobe which allows patients to preserve their self dignity and to enhance their quality of life.

Due to the frail condition of many patients, they spend a substantial part of each day in a seated position with the assistance of various support devices or restraint devices such as seating cushions. Current seating cushions are either expensive custom made devices or part of a series of stock cushions, neither of which functions as an integrated seating cushion system which can provide supplemental support for a range of patient sizes or for a range of chair sizes and types. A need exists for a modular seating cushion system that functions in combination with a belt system with various chair sizes and types, and in combination with a belt system and a garment system with various chair sizes and types, to allow the caregiver to easily configure a "custom" seating environment to assist in satisfying the medical and safety needs of each patient.

The humane and effective care of patients requires an adaptive patient support and restraint system which provides an ergonomically friendly interface which is safe and comfortable to use, and which allows patients to maintain their self dignity and to be free of unnecessary physical restraint. Therefore, a need exists for an adaptive support and restraint system that provides selectively interchangeable, adjustable, variable, and distributive physical support and physical restraint, and that enhances the quality of life for patients using the system.

SUMMARY OF THE INVENTION

According to the present invention, an adaptive patient support and restraint system for controlling movement of a patient comprising a belt system, a garment system, and a seating cushion system is provided. In one embodiment, the adaptive patient support and restraint system comprises a pelvic support and one or more differently shaped belts that are selectively configurable and interconnectable on the patient and a chair for controlling movement of the patient. The patient's movement is controlled by selectably supporting the patient in the chair, selectably restraining the patient in the chair, or selectably supporting and selectably restraining the patient in the chair as required by the patient's particular medical or safety needs. In addition, the pelvic support and the one or more differently shaped belts are configurable and interconnectable for controlling movement of the patient by variably supporting the patient in the chair, variably restraining the patient in the chair, or variably supporting and variably restraining the patient in the chair as required to compensate for changes in the patient's medical or safety needs. In another embodiment, the adaptive patient support and restraint system comprises one or more garments and one or more differently shaped belts that are selectively configurable and interconnectable on the patient and a chair or a bed for controlling movement of the patient as required by particular medical or safety needs, and to cover the patient's body. In still another embodiment, the adaptive patient support and restraint system comprises one or more garments and a bed restraint belt that are selectively configurable and interconnectable on the patient and a bed for restraining movement of the patient in the bed. In still another embodiment, the adaptive patient support system comprises side support cushions, shoulder bolster cushions, a headrest cushion, a back support cushion, and a wedge seat cushion for supporting a patient in a chair. The side support cushions are selectively configurable on the arms of the chair, and the shoulder bolster cushions are selectively configurable on the side support cushions, for selectably supporting either or both of the patient's sides. The headrest cushion is interconnectable with the chair back using one or more belts for supporting the patient's head. The back support cushion is interconnectable with the chair back using one or more belts for supporting the patient's back. The wedge seat cushion is configurable on the top of the chair seat for supporting the patient's legs.

BRIEF DESCRIPTION OF THE DRAWINGS

In the accompanying drawings, which are incorporated in and constitute a part of this specification, embodiments of the invention are illustrated, which, together with a general description of the invention given above, and the detailed description given below serve to exemplify the principles of this invention.

FIG. 1A and FIG. 1B, taken together, illustrate the belts and pelvic support used in various embodiments of the present invention;

FIG. 3 is a front view of the belt system providing lower body support and a medium level of upper body support in a gerichair;

FIG. 4 is a rear view of the belt system as selectively configured in FIG. 3 for providing lower body support and a medium level of upper body support in a gerichair;

FIG. 11A and FIG. 11B, taken together, illustrate the garments comprising the garment system of the present invention;

FIG. 23 is a front view of the side support cushions, shoulder bolster cushions, headrest cushion, and wedge seat cushion being used in combination with the belt system in a gerichair;

FIG. 24 is a rear side view of the side support cushions, shoulder bolster cushions, headrest cushion, and wedge seat cushion as selectively configured in FIG. 23 being used in combination with the belt system in a gerichair;

DETAILED DESCRIPTION OF THE PREFERRED EMBODIMENT

Figure 1A:
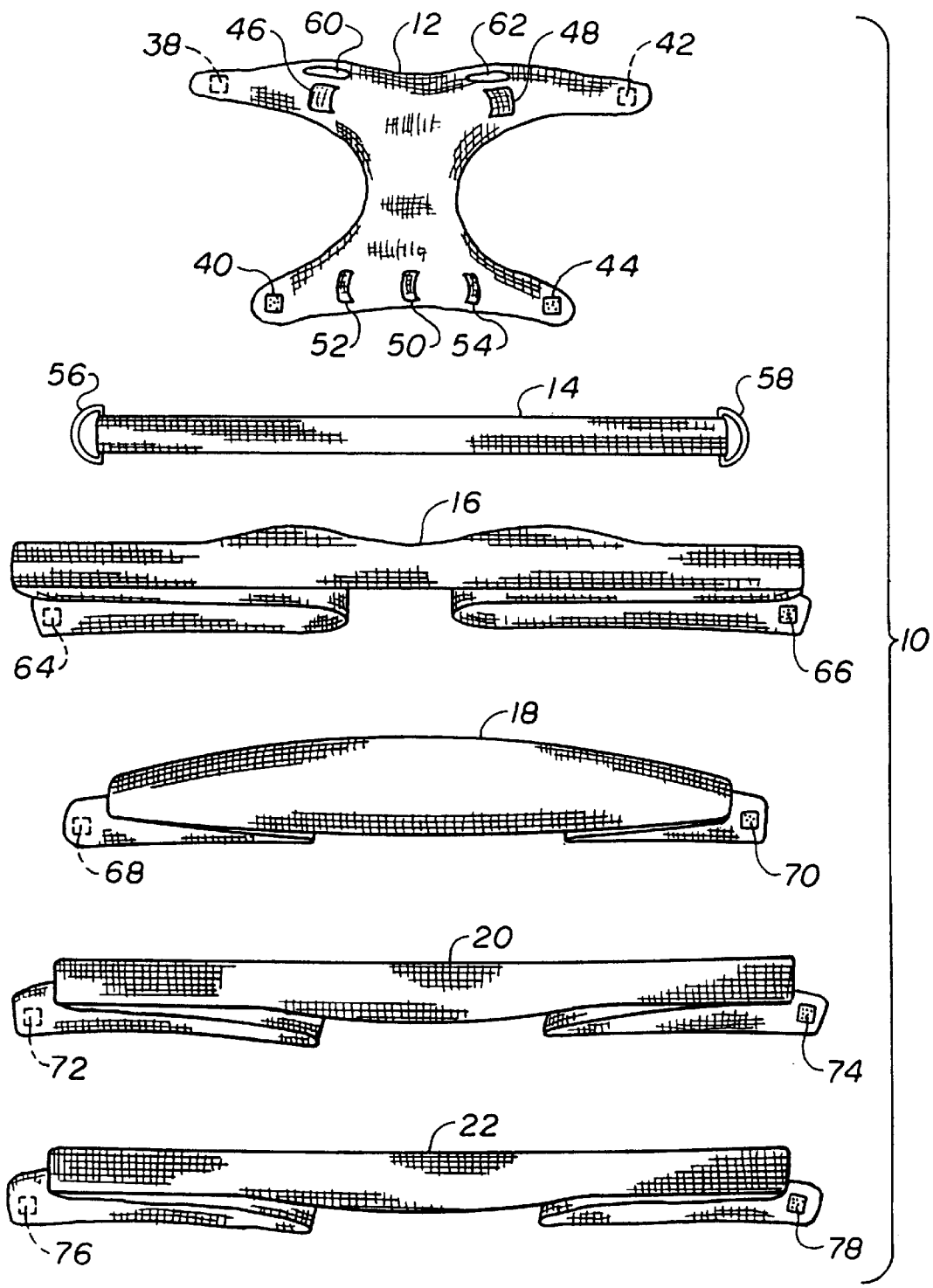

According to the present invention, an adaptive patient support and restraint system that provides (i) selective interchangeable delivery of physical support, physical restraint, or physical support and physical restraint to control movement of the upper body and to control movement of the lower body, (ii) adjustable delivery of physical support, physical restraint, or physical support and physical restraint to accommodate a range of patient sizes, various chair sizes and types, various gerichair sizes and types, and various wheelchair sizes and types, (iii) variable level delivery of physical support, physical restraint, or physical support and physical restraint to accommodate a range of patient medical and safety needs, and (iv) distributive delivery of physical support, physical restraint, or physical support and physical restraint to distribute stresses associated with support and restraint over a broad area of a patient's body, is disclosed. The adaptive patient support and restraint system includes a belt system, a garment system, and seating cushion system. The belt system can be used as a stand-alone system, in combination with the garment system, in combination with the seating cushion system, or in combination with the garment system and the seating cushion system to provide the degree of physical control necessary to accommodate the medical and safety requirements of a range of patients and to enhance each patient's quality of life. As described herein, the term "patient" refers generally to an elderly person or other person requiring physical support or physical restraint for medical or safety purposes.

The adaptive patient support and restraint system can be selectively interchanged on a patient so as to provide interchangeable support and restraint to control movement of the patient's upper body and to control movement of the patient's lower body. Further, the system can be adjusted for use with different size patients in various chair sizes and types. Still further, the system can be configured to deliver variable levels of patient control to satisfy a range of patient medical and safety needs. Still further, the system can distribute the stresses associated with physical support and physical restraint over a broad area of a patient's body.

The belt system assists in preventing a patient who is seated in a chair, a gerichair, or a wheelchair from sliding down in the chair, falling out of the chair, leaning from side to side in the chair, or falling forward in the chair. In addition, the belt system allows a patient who is seated in a chair, a gerichair, or a wheelchair, or who is lying or seated in a bed, to experience a moderate range of natural freedom of movement while being physically supported, physically restrained, or physically supported and physically restrained, unlike the prior support and restraint systems. The range of natural freedom of movement allows the patient to obtain some passive exercise of at least some parts of his body while being safely supported or restrained.

The garment system can be used in combination with the belt system to distribute the stresses associated with physical support and physical restraint over a large area of a patient's body to minimize any patient discomfort when being supported or restrained and to reduce the risk of skin irritation, neither of which is provided in the prior support and restraint systems. The seating cushion system provides supplemental support for further enhancing the patient's overall comfort level which is not provided in the prior support and restraint systems.

FIG. 1A and FIG. 1B, taken together, illustrate the components of Belt System 10 for providing adaptive patient support and restraint in the multiple embodiments of the belt system of the present invention. Belt System 10 includes Pelvic Support 12, Pelvic Support Belt 14, Lap Belt 16, Anchor Belt 18, Chest Belt 20, Chest Belt 22, Shoulder Belt 24, Shoulder Belt 26, Torso Belt 28, Torso Belt 30, Chair Handle Belt 32, Lashing Belt 34, and Bed Restraint Belt 36. In various applications of the inventive adaptive patient support and restraint system, specific combinations of less than all of the components of Belt System 10 are used. Examples of these various applications are described with respect to FIGS. 2–10 and FIGS. 12–28.

Each of the component belts of Belt System 10 except Pelvic Support Belt 14 and Chair Handle Belt 32 are provided with one or more complementary fastener pairs which permit a portion of the belt having one of the fasteners of a fastener pair to be attached to a portion of the belt having the other fastener of that complementary fastener pair. In addition, Pelvic Support 12 is provided with two complementary fastener pairs which permit Pelvic Support 12 to be easily positioned on a patient and to be easily removed from a patient. Fasteners such as hook-type fasteners and loop-type fasteners can be used as complementary fastener pairs as shown in FIG. 1A and FIG. 1B for Pelvic Support 12, Lap Belt 16, Anchor Belt 18, Chest Belt 20, Chest Belt 22, Shoulder Belt 24, Shoulder Belt 26, Torso Belt 28, Torso Belt 30, Lashing Belt 34, and Bed Restraint Belt 36. However, it is contemplated that fasteners other than hook-type fasteners and loop-type fasteners can be used in implementing Belt System 10. As used hereinafter, the term "fastener" is meant to include any type of fastener and is specifically not limited to the representative hook-type fasteners and loop-type fasteners as shown in FIG. 1A and FIG. 1B. It is to be appreciated that while the two fasteners of a given complementary fastener pair must be able to connect with one another, there is no requirement that one fastener (e.g., a hook-type fastener) be placed at only a first complementary fastener pair site location and that the other fastener (e.g., the loop-type fastener) be placed at only a second complementary fastener pair site location. For example, as shown in FIG. 1A for Lap Belt 16, Fastener 64 can be a hook-type fastener and Fastener 66 can be a loop-type fastener, or, alternatively, Fastener 64 can be a loop-type fastener and Fastener 66 can be a hook-type fastener. It is to be further appreciated that while the complementary fastener pairs of FIG. 1A and FIG. 1B are shown providing a limited range of adjustability, a greater range of adjustability is contemplated by, for example, using a long strip of a hook-type fastener, using a long strip of a loop-type fastener, or using both a long strip of a hook-type fastener and a long strip of a loop-type fastener for each of the complementary fastener pairs.

Pelvic Support 12, Pelvic Support Belt 14, Lap Belt 16, Anchor Belt 18, Chest Belt 20, Chest Belt 22, Shoulder Belt 24, Shoulder Belt 26, Torso Belt 28, Torso Belt 30, Chair Handle Belt 32, and Lashing Belt 34 are preferred to be made of materials that are soft, stretchable, strong, washable, and that can be dyed in various colors and printed with designs and essential information, and that can be made in different sizes and different lengths to satisfy various patient sizes, various chair sizes and types, various gerichair sizes and types, and various wheelchair sizes and types. Further, Belt System 10 is preferred to be color-coded to allow the caregiver to easily determine the configuration and interconnection of Belt System 10 with the patient and a chair or a bed, and with Garment System 150 and Seating Cushion System 250.

Pelvic Support 12 functions in a chair application, a gerichair application, or a wheelchair application to support a patient's lower body to prevent the patient from sliding down in, or from sliding out of, the chair, gerichair, or wheelchair. Further, Pelvic Support 12 functions to support or restrain a patient in a chair, a gerichair, or a wheelchair application to prevent the patient from exiting the seat and injuring himself or someone else. It is to be appreciated that Pelvic Support 12 can be made in various sizes to accommodate a range of patient physical sizes. It is to be further appreciated that Pelvic Support 12 can be configured with alternative belt loop arrangements to allow it to be used with different chairs, gerichairs, or wheelchairs, and with coordinated clothing.

Figure 2:
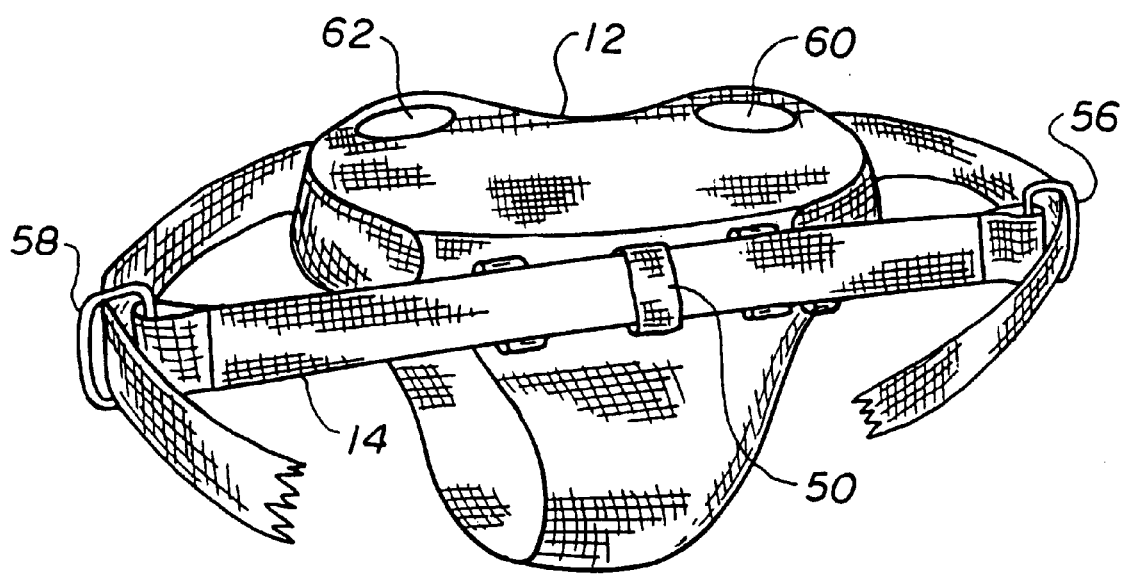
FIG. 2 illustrates the pelvic support device shown as can be configured about a patient's waist area.

FIG. 2 shows one of the multiple applications of the inventive adaptive patient restraint and support system. Pelvic Support 12, Pelvic Support Belt 14, and Lap Belt 16 can function in multiple applications to support or restrain a patient's lower body. Pelvic Support 12 is configured to be positioned between the patient's legs and around the patient's waist area. Pelvic Support 12 includes Fasteners 38, 40 and Fasteners 42, 44 for securing Pelvic Support 12 with the patient. Fastener 38 is connected with Fastener 40 along the right side of the patient's waist area, and Fastener 42 is connected with Fastener 44 along the left side of the patient's waist area. Fasteners 38, 40 and Fasteners 42, 44 are preferred to be made of a hook-and-loop type material to allow the caregiver to easily position Pelvic Support 12 around the patient's waist, to easily remove Pelvic Support 12, and to easily adjust Pelvic Support 12 for different patient sizes. It is to be appreciated that Pelvic Support 12 can be made in various sizes of shorts and thereby eliminate Fasteners 38, 40 and Fasteners 42, 44 from Pelvic Support 12. In a gerichair application, Belt Loops 46, 48 receive Lap Belt 16 in front of the patient, and Belt Loop 50 receives Pelvic Support Belt 14 behind the patient. In a bed application, Belt Loops 46, 48 receive Bed Restraint Belt 36 in front of the patient and Belt Loop 50 receives Bed Restraint Belt 36 behind the patient. It is to be appreciated that alternative embodiments of the configuration of belt loops on Pelvic Support 12 can be used to satisfy strength, stability, and interconnection requirements for differing patient sizes, as well as for various chair sizes and types, various gerichair sizes and types, and various wheelchair sizes and types. For example, Belt Loops 52, 54 receive Lap Belt 16 along the rear of the wheelchair back in a wheelchair application. Pelvic Support Belt 14 supplements the control provided by Pelvic Support 12 and Lap Belt 16 in a chair application or a wheelchair application. Pelvic Support Belt 14 is first positioned behind the patient and passes through Belt Loop 50 at the rear center waist section of Pelvic Support 12, and thereafter Lap Belt 16 also passes through D-Ring 56 along the right side of the patient and through D-Ring 58 along the left side of the patient. Eyelets 60, 62 receive Torso Belts 28, 30 along the front waist area of the patient to provide the maximum level of upper body control. Lap Belt 16 includes Fasteners 64, 66 which are connected together for securing Lap Belt 16 around the patient and a chair back, a gerichair back, or a wheelchair back. Fasteners 64, 66 are preferred to be fabricated from a hook-and-loop type material to allow the caregiver to easily position Lap Belt 16 around the patient and the gerichair back, and to easily adjust the length of Lap Belt 16 for a range of patient sizes and for various gerichair sizes and types. Fastener 64 can be connected with Fastener 66 in front of the patient, or otherwise within the patient's reach, such that Lap Belt 16 functions to physically support the patient (not shown). Alternatively, Fastener 64 can be connected with Fastener 66 behind the patient, or otherwise outside of the patient's reach, such that Lap Belt 16 functions to physically restrain the patient (not shown).

FIG. 3 and FIG. 4 show another of the multiple applications of the inventive adaptive patient restraint and support system. Pelvic Support 12, Pelvic Support Belt 14, and Lap Belt 16 can function to provide lower body support or lower body restraint in a gerichair application. Pelvic Support 12 is positioned on the patient by positioning the front section of Pelvic Support 12 along the front of the patient's waist, positioning the center section of Pelvic Support 12 between the patient's legs, and positioning the rear section of Pelvic Support 12 along the rear of the patient's waist. Pelvic Support 12 is secured around the patient's waist by connecting Fastener 38 with Fastener 40 along the right side of the patient's waist area, and by connecting Fastener 42 with Fastener 44 along the left side of the patient's waist area. Pelvic Support Belt 14 is positioned behind the patient and passes through Belt Loop 50 of Pelvic Support 12 with D-Ring 56 being positioned along the right side of the patient and D-Ring 58 being positioned along the left side of the patient. For controlling movement of the patient's lower body, Lap Belt 16 is passed through Belt Loop 46 along the front right waist area of the patient, passed through D-Ring 56 along the right side of the patient, passed around the rear of the gerichair back, passed through D-Ring 58 along the left side of the patient, and passed through Belt Loop 48 along the front left waist area of the patient. Fastener 64 is connected with Fastener 66 to secure Lap Belt 16. Fastener 64 is connected with Fastener 66 in front of the patient, or otherwise within the patient's reach, such that Pelvic Support 12, Pelvic Support Belt 14, and Lap Belt 16 function to physically support the patient's body. Alternatively, Fastener 64 is connected with Fastener 66 behind the gerichair back, or otherwise outside of the patient's reach, such that Pelvic Support 12, Pelvic Support Belt 14, and Lap Belt 16 function to physically restrain the patient's body (not shown). Anchor Belt 18 functions to anchor Lap Belt 16 to the gerichair structure for limiting movement of Lap Belt 16. Anchor Belt 18 is first passed around Lap Belt 16 along the rear of the gerichair back, and then passed around a cross-member of the gerichair. Fastener 68 is connected with Fastener 70 along the rear of the gerichair back to secure Anchor Belt 18 so as to anchor Lap Belt 16 in a substantially fixed position on the gerichair. Fasteners 68, 70 are preferred to be fabricated from a hook-and-loop type material to allow the caregiver to easily position and secure Anchor Belt 18 around Lap Belt 16 and around the gerichair cross-member, and to allow the caregiver to easily adjust the length of Anchor Belt 18 for different gerichair sizes.

Figure 6:
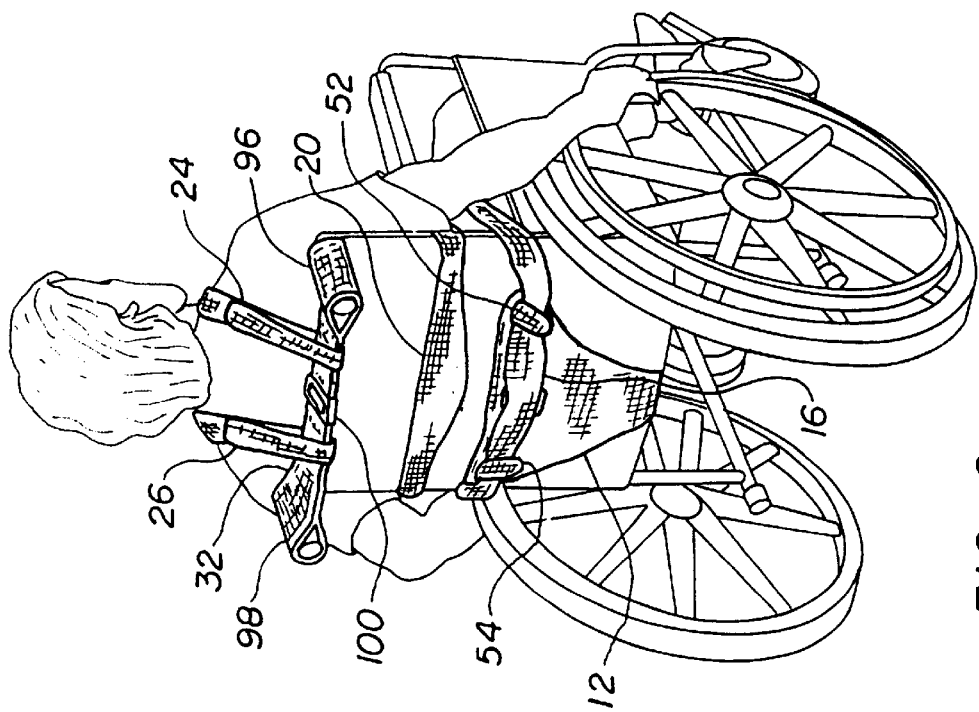
FIG. 6 is a rear view of the belt system as selectively configured in FIG. 5 for providing lower body support and a medium level of upper body support in a wheelchair.
Figure 5:
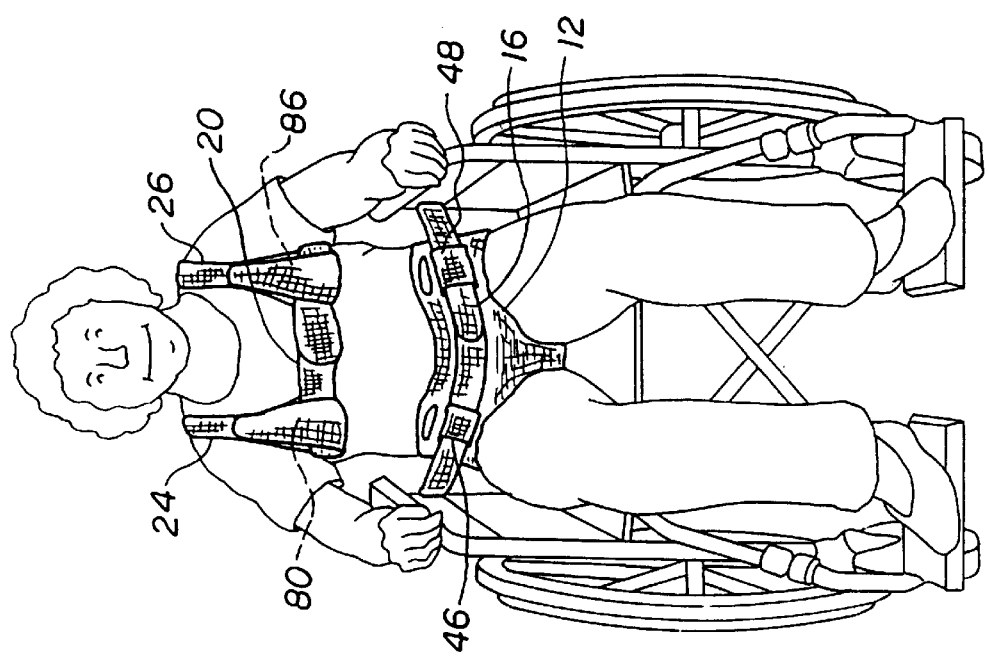
FIG. 5 is a front view of the belt system providing lower body support and a medium level of upper body support in a wheelchair.

FIG. 5 and FIG. 6 show another of the multiple applications of the inventive adaptive patient restraint and support system. Pelvic Support 12 and Lap Belt 16 can function to provide body support or body restraint in a wheelchair application. Pelvic Support 12 is positioned on the patient by positioning the front section of Pelvic Support 12 along the front of the patient's waist, positioning the center section of Pelvic Support 12 between the patient's legs, passing the rear section of Pelvic Support 12 through an opening between the wheelchair back and the wheelchair seat, and positioning the rear section of Pelvic Support 12 along the rear of the wheelchair back. For controlling movement of the patient's body, Lap Belt 16 is passed through Belt Loops 46 along the front right waist area of the patient, passed through Belt Loop 52 along the rear right section of the wheelchair back, passed through Belt Loop 54 along the rear left section of the wheelchair back, and passed through Belt Loop 48 along the front left waist area of the patient. Fastener 64 is connected with Fastener 66 to secure Lap Belt 16. Fastener 64 is connected with Fastener 66 in front of the patient, or otherwise within the patient's reach, such that Pelvic Support 12 and Lap Belt 16 function to physically support the patient's body. Alternatively, Fastener 64 is connected with Fastener 66 behind the wheelchair back, or otherwise outside of the patient's reach, such that Pelvic Support 12 and Lap Belt 16 function to physically restrain the patient's body (not shown).

Belt System 10 functions to provide three levels of upper body support or upper body restraint: minimum, medium, and maximum. It is preferred that the patient be prevented from sliding down in the chair, as described above, to minimize the risk of strangulation or other personal injury when using any one of the three levels of upper body support or upper body restraint. By supporting the patient's body, Belt System 10 functions to prevent the patient from sliding down in a chair, a gerichair, or a wheelchair. By restraining the patient's body, Belt System 10 functions to prevent the patient from sliding down in a chair, a gerichair, or a wheelchair, and to prevent the patient from otherwise leaving the chair, the gerichair, or the wheelchair.

Chest Belt 20 is used in chair applications, in gerichair applications, and in wheelchair applications to control movement of the patient's upper body relative to a chair back, a gerichair back, or a wheelchair back for all three levels of upper body support or upper body restraint. In a wheelchair application, Chest Belt 20 is passed along the front of the patient's chest and under the patient's arm pits and along the rear of the wheelchair back, and Fastener 72 is connected with Fastener 74 to secure Chest Belt 20 around both the patient's upper body and the wheelchair back. In a chair application or a gerichair application, Chest Belt 20 is passed along the front of the patient's chest and under the patient's arm pits and along either the rear of the chair back or the gerichair back, and Fastener 72 is connected with Fastener 74 to secure Chest Belt 20 around both the patient's upper body and either the chair back or the gerichair back. Fastener 72 can be connected with Fastener 74 in front of the patient, or otherwise within the patient's reach, such that Chest Belt 20 functions to physically support the patient. Alternatively, Fastener 72 can be connected with Fastener 74 behind the patient, or otherwise outside of the patient's reach, such that Chest Belt 20 functions to physically restrain the patient.

Belt System 10 and Garment System 150 can function together in a wheelchair application, and, in one such wheelchair application, Chest Belt 20 and Chest Belt 22 are used concurrently to provide upper body restraint. Chest Belt 20 is secured by connecting Fastener 72 with Fastener 74, and Chest Belt 22 is secured by connecting Fastener 76 with Fastener 78, as described below. Fasteners 72, 74 and Fasteners 76, 78 are preferred to be made of hook-and-loop type material to allow the caregiver to easily position Chest Belt 20 and Chest Belt 22, and to allow the caregiver to easily adjust the length of Chest Belt 20 and Chest Belt 22. Chest Belt 20 and Chest Belt 22 are functionally identical to one another and physically identical to one another, and can be used interchangeably.

To provide a minimum level of upper body support or upper body restraint in a chair application, a gerichair application, or a wheelchair application, Chest Belt 20 functions to control movement of the patient's upper body relative to a chair back, a gerichair back, or a wheelchair back. Chest Belt 20 is positioned along the front of the patient's chest, under the patient's arm pits, along the rear of either a chair back, a gerichair back, or a wheelchair back, and Fastener 72 is connected with Fastener 74 to secure Chest Belt 20 around both the patient's upper body and the rear of the chair back, the gerichair back, or the wheelchair back. Fastener 72 is connected with Fastener 74 in front of the patient, or otherwise within the patient's reach, such that Chest Belt 20 functions to provide the patient with a minimum level of upper body support. Alternatively, Fastener 72 is connected with Fastener 74 behind either the chair back, the gerichair back, or the wheelchair back, or otherwise outside of the patient's reach, such that Chest Belt 20 functions to provide the patient with a minimum level of upper body restraint. The minimum level of upper body support or upper body restraint functions to prevent the patient from falling forward in a chair, a gerichair, or a wheelchair, and is complemented by the body support or body restraint at the waist, as described above.

To provide a medium level of upper body support or upper body restraint in a chair application or a gerichair application, Chest Belt 20, Shoulder Belt 24, Shoulder Belt 26, and Lashing Belt 34 function to control movement of the patient's upper body relative to a chair back or a gerichair back. Shoulder Belt 24 and Shoulder Belt 26 are physically identical to one another and functionally identical to one another, and can be used interchangeably over either the patient's right shoulder or the patient's left shoulder. Shoulder Belt 24 includes Belt Receiver 80 at the first end and Fasteners 82, 84 at the second end. Shoulder Belt 26 includes Belt Receiver 86 at the first end and Fasteners 88, 90 at the second end. Belt Receiver 80 and Belt Receiver 86 are sufficiently large to allow Chest Belt 20 to be easily passed therethrough. Fasteners 82, 84 and Fasteners 88, 90 are preferred to be made of hook-and-loop type material to allow the caregiver to easily interconnect Shoulder Belt 24 with Chest Belt 20 or Chair Handle Belt 32 and to easily interconnect Shoulder Belt 26 with Chest Belt 20 or Chair Handle Belt 32, respectively, and to allow the caregiver to easily adjust the length of Shoulder Belt 24 and the length of Shoulder Belt 26 to conform with a range of patient sizes and with various chair sizes and types, various gerichair sizes and types, and various wheelchair sizes and types. Lashing Belt 34 includes Fastener 92 at one end and Fastener 94 at the other end. Lashing Belt 34 is passed around Shoulder Belt 24 and around Shoulder Belt 26 along either the rear of a chair back or the rear of a gerichair back. Fastener 92 is connected with Fastener 94 to maintain Shoulder Belt 24 and Shoulder Belt 26 in a substantially fixed position relative to one another to prevent Shoulder Belt 24 and Shoulder Belt 26 from falling off either the sides of the chair back or the sides of the gerichair back, and from falling off the patient's shoulders. Fasteners 92, 94 are preferred to be made of hook-and-loop type material to allow the caregiver to easily position Lashing Belt 34 and to easily connect Lashing Belt 34 to interconnect Shoulder Belt 24 and Shoulder Belt 26 or to interconnect Torso Belt 28 and Torso Belt 30, and to allow the caregiver to easily adjust the length of Lashing Belt 34 to conform with a range of patient sizes, with various chair sizes and types, and with various gerichair sizes and types.

FIG. 3 and FIG. 4 show another of the multiple applications of the inventive adaptive patient restraint and support system. Chest Belt 20, Shoulder Belt 24, Shoulder Belt 26, and Lashing Belt 34 can function to control movement of the patient's upper body relative to a gerichair back in a gerichair application. Shoulder Belt 24 is positioned along the front right side of the patient's chest, over the patient's right shoulder, over the top of the gerichair back, and along the rear right section of the gerichair back. Shoulder Belt 26 is positioned along the front left side of the patient's chest, over the patient's left shoulder, over the top of the gerichair back, and along the rear left section of the gerichair back. Chest Belt 20 is passed through Belt Receiver 80 along the front right side of the patient's chest, passed around the rear of the gerichair back so as to be positioned over the second end of Shoulder Belt 24 and over the second end of Shoulder Belt 26 at the rear of the gerichair back, and passed through Belt Receiver 86 along the front left side of the patient's chest. Fastener 82 is connected with Fastener 84 to interconnect Shoulder Belt 24 with Chest Belt 20 at the rear right section of the gerichair back. Fastener 88 is connected with Fastener 90 to interconnect Shoulder Belt 26 with Chest Belt 20 at the rear left section of the gerichair back. Fastener 72 is connected with Fastener 74 to complete the interconnection of Chest Belt 20 with Shoulder Belt 24 and Shoulder Belt 26. Lashing Belt 34 is passed around Shoulder Belt 24 and around Shoulder Belt 26 along the rear of the gerichair back. Fastener 92 is connected with Fastener 94 to maintain Shoulder Belt 24 and Shoulder Belt 26 in a substantially fixed position relative to one another to assist in preventing Shoulder Belt 24 and Shoulder Belt 26 from falling off the sides of the gerichair back, and from falling off the patient's shoulders. Fastener 72 is connected with Fastener 74 in front of the patient, or otherwise within the patient's reach, such that Chest Belt 20, Shoulder Belt 24, Shoulder Belt 26, and Lashing Belt 34 function to provide the patient with a medium level of upper body support. Alternatively, Fastener 72 is connected with Fastener 74 behind the gerichair back, or otherwise outside of the patient's reach, such that Chest Belt 20, Shoulder Belt 24, Shoulder Belt 26, and Lashing Belt 34 function to provide the patient with a medium level of upper body restraint (not shown). The medium level of upper body support or upper body restraint functions to prevent the patient from falling to one side or the other in a gerichair, to prevent the patient from falling forward in a gerichair, and to prevent the patient from getting out of a gerichair seat, and is complemented by the body support or body restraint at the waist, as described above.

To provide a medium level of upper body support or upper body restraint in a wheelchair application, Chest Belt 20, Shoulder Belt 24, Shoulder Belt 26, and Chair Handle Belt 32 function to control movement of the patient's upper body relative to a wheelchair back. Chair Handle Belt 32 includes Chair Handle Receiver 96 and Chair Handle Receiver 98 for attaching Chair Handle Belt 32 to the two handles at the upper rear section of the wheelchair. Chair Handle Receivers 96, 98 are sufficiently large to allow the wheelchair handles to be easily passed therethrough for easy attachment of Chair Handle Belt 32 to the wheelchair. In an alternative embodiment, Chair Handle Belt 32 can also be configured with Adjuster 100 to allow the caregiver to easily adjust the length of Chair Handle Belt 32 for use with various wheelchair sizes and types. Shoulder Belt 24 and Shoulder Belt 26 interconnect with Chair Handle Belt 32 between the two handles at the upper rear section of the wheelchair back.

FIG. 5 and FIG. 6 show another of the multiple applications of the inventive adaptive patient restraint and support system. Chest Belt 20, Shoulder Belt 24, Shoulder Belt 26, and Chair Handle Belt 32 can function to control movement of the patient's upper body relative to a wheelchair back in a wheelchair application. Shoulder Belt 24 is positioned along the front right side of the patient's chest, over the patient's right shoulder, over the wheelchair back, and along the rear right section of the wheelchair back. Shoulder Belt 26 is positioned along the front left side of the patient's chest, over the patient's left shoulder, over the wheelchair back, and along the rear left section of the wheelchair back. Chair Handle Belt 32 is attached to the two handles at the upper rear section of the wheelchair. Fastener 82 is connected with Fastener 84 to interconnect Shoulder Belt 24 with Chair Handle Belt 32 between the two handles at the upper rear section of the wheelchair back. Fastener 88 is connected with Fastener 90 to interconnect Shoulder Belt 26 with Chair Handle Belt 32 between the two handles at the upper rear section of the wheelchair back. Chest Belt 20 is passed through Belt Receiver 80 along the front right side of the patient's chest, passed around the rear of the wheelchair back, and passed through Belt Receiver 86 along the front left side of the patient's chest. Alternatively, Chest Belt 20 is passed through Belt Receiver 80 along the front right side of the patient's chest, passed around the patient's back, and passed through Belt Receiver 86 along the front left side of the patient's chest. In either arrangement, Fastener 72 is connected with Fastener 74 to complete the interconnection of Chest Belt 20 with Shoulder Belt 24 and Shoulder Belt 26. Fastener 72 is connected with Fastener 74 in front of the patient, or otherwise within the patient's reach, such that Chest Belt 20, Shoulder Belt 24, Shoulder Belt 26, and Chair Handle Belt 32 function to provide the patient with a medium level of upper body support. Alternatively, Fastener 72 is connected with Fastener 74 behind the patient or behind the wheelchair back, or otherwise outside of the patient's reach, such that Chest Belt 20, Shoulder Belt 24, Shoulder Belt 26, and Chair Handle Belt 32 function to provide the patient with a medium level of upper body restraint (not shown). The medium level of upper body support or upper body restraint functions to prevent the patient from falling to one side or the other in a wheelchair, to prevent the patient from falling forward in a wheelchair, and to prevent the patient from getting out of a wheelchair seat, and is complemented by the body support or body restraint at the waist, as described above.

To provide a maximum level of upper body support or upper body restraint in a chair application or a gerichair application, Pelvic Support 12, Chest Belt 20, Torso Belt 28, Torso Belt 30, and Lashing Belt 34 function to control movement of the patient's upper body relative to a chair back or a gerichair back. Torso Belt 28 and Torso Belt 30 are physically identical to one another and functionally identical to one another, and can be used interchangeably over either the patient's right shoulder or the patient's left shoulder. Torso Belt 28 includes Belt Loop 102, Fasteners 104, 106 at the first end, and Fasteners 108, 110 at the second end. Torso Belt 30 includes Belt Loop 112, Fasteners 114, 116 at the first end, and Fasteners 118, 120 at the second end. Belt Loop 100 and Belt Loop 112 are sufficiently large to allow Chest Belt 20 to be easily passed therethrough. Fasteners 104, 106 and Fasteners 114, 116 are preferred to be made of hook-and-loop type material to allow the caregiver to easily interconnect Torso Belt 28 with Eyelet 60 of Pelvic Support 12 and Torso Belt 30 with Eyelet 62 of Pelvic Support 12, respectively, and to allow the caregiver to easily adjust the length of Torso Belt 28 and the length of Torso Belt 30 to conform with a range of patient sizes, and with various chair sizes and types, various gerichair sizes and types, and various wheelchair sizes and types. Fasteners 108, 110 and Fasteners 118, 120 are preferred to be made of hook-and-loop type material to allow the caregiver to easily interconnect Torso Belt 28 with Chest Belt 20 or Chair Handle Belt 32 and to easily interconnect Torso Belt 30 with Chest Belt 20 or Chair Handle Belt 32, respectively, and to easily adjust the length of Torso Belt 28 and the length of Torso Belt 30 to conform with a range of patient sizes and with various chair sizes and types, various gerichair sizes and types, and various wheelchair sizes and types. Lashing Belt 34 is passed around Torso Belt 28 and around Torso Belt 30 along the rear of the gerichair back. Fastener 92 is connected with Fastener 94 to maintain Torso Belt 28 and Torso Belt 30 in a substantially fixed position relative to one another to prevent Torso Belt 28 and Torso Belt 30 from falling off either the sides of the chair back or the sides of the gerichair back, and from falling off the patient's shoulders.

Figure 8:
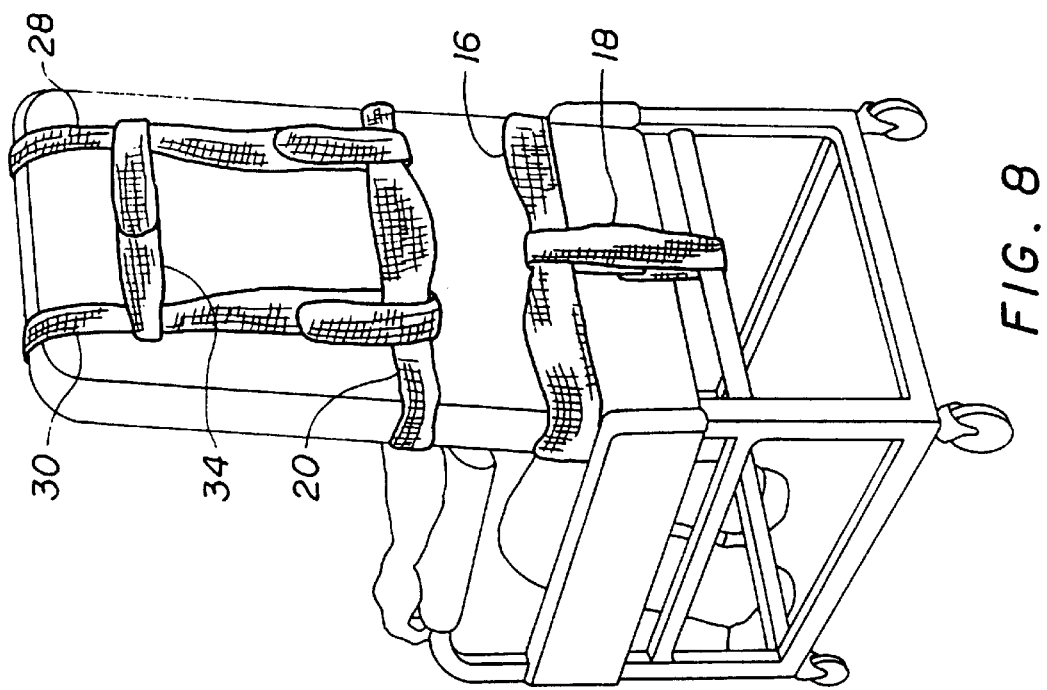
FIG. 8 is a rear view of the belt system as selectively configured in FIG. 7 for providing lower body support and a maximum level of upper body support in a gerichair.
Figure 7:
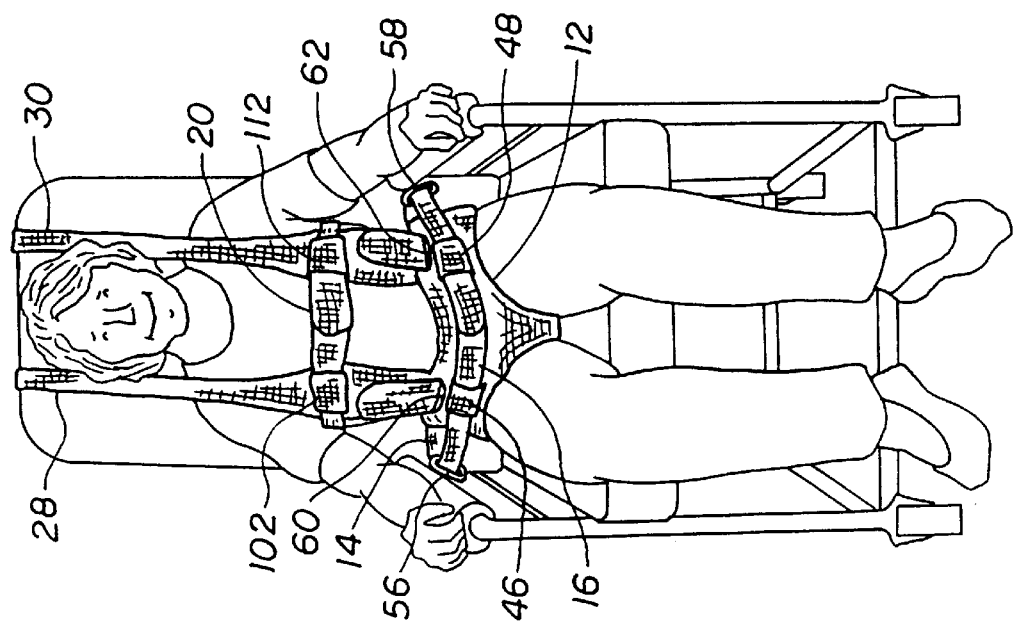
FIG. 7 is a front view of the belt system providing lower body support and a maximum level of upper body support in a gerichair.

FIG. 7 and FIG. 8 show another of the multiple applications of the inventive adaptive patient restraint and support system. Pelvic Support 12, Chest Belt 20, Torso Belt 28, Torso Belt 30, and Lashing Belt 34 can function to control movement of the patient's upper body relative to a gerichair back in a gerichair application. Pelvic Support 12 is positioned on the patient by positioning the front section of Pelvic Support 12 along the front of the patient's waist, positioning the center section of Pelvic Support 12 between the patient's legs, and positioning the rear section of Pelvic Support 12 along the rear of the patient's waist. Pelvic Support 12 is secured around the patient's waist by connecting Fastener 38 with Fastener 40 along the right side of the patient's waist area, and by connecting Fastener 42 with Fastener 44 along the left side of the patient's waist area. Torso Belt 28 is positioned along the front right side of the patient's chest, over the patient's right shoulder, over the top of the gerichair back, and along the rear right section of the gerichair back. Torso Belt 30 is positioned along the front left of the patient's chest, over the patient's left shoulder, over the top of the gerichair back, and along the rear left section of the gerichair back. Torso Belt 28 interconnects with Pelvic Support 12 at the front right waist area of the patient by first passing the first end of Torso Belt 28 through Eyelet 60, and then connecting Fastener 108 with Fastener 110 together to form the interconnection. Torso Belt 30 interconnects with Pelvic Support 12 at the front left waist area of the patient by first passing the first end of Torso Belt 30 through Eyelet 62, and then connecting Fastener 118 with Fastener 120 to form the interconnection. Chest Belt 20 is passed through Belt Loop 102 along the front right side of the patient's chest, passed around the rear of the gerichair back so as to be positioned over the second end of Torso Belt 28 and the second end of Torso Belt 30 at the rear of the gerichair back, and passed through Belt Loop 112 along the front left side of the patient's chest. Fastener 108 is connected with Fastener 110 to interconnect Torso Belt 28 with Chest Belt 20 at the rear right section of the gerichair back. Fastener 118 is connected with Fastener 120 to interconnect Torso Belt 30 with Chest Belt 20 at the rear left section of the gerichair back. Fastener 72 is connected with Fastener 74 to complete the interconnection of Chest Belt 20 with Torso Belt 28 and Torso Belt 30. Lashing Belt 34 is passed around Torso Belt 28 and around Torso Belt 30 along the rear of the gerichair back. Fastener 92 is connected with Fastener 94 to maintain Torso Belt 28 and Torso Belt 30 in a substantially fixed position relative to one another to prevent Torso Belt 28 and Torso Belt 30 from falling off the sides of the gerichair back, and from falling off the patient's shoulders. Fastener 72 is connected with Fastener 74 in front of the patient, or otherwise within the patient's reach, such that Pelvic Support 12, Chest Belt 20, Torso Belt 28, Torso Belt 30, and Lashing Belt 34 function to provide the patient with a maximum level of upper body support. Alternatively, Fastener 72 is connected with Fastener 74 behind the gerichair back, or otherwise outside of the patient's reach, such that Pelvic Support 12, Chest Belt 20, Shoulder Belt 24, Shoulder Belt 26, and Lashing Belt 34 function to provide the patient with a maximum level of upper body restraint (not shown). The maximum level of upper body support or upper body restraint functions to prevent the patient from falling to one side or the other in a gerichair, to prevent the patient from falling forward in a gerichair, and to prevent the patient from getting out of a gerichair seat, and is complemented by the body support or body restraint at the waist, as described above.

To provide a maximum level of upper body support or upper body restraint in a wheelchair application, Pelvic Support 12, Chest Belt 20, Torso Belt 28, Torso Belt 30, and Chair Handle Belt 32 function to control movement of the patient's upper body relative to a wheelchair back. Chair Handle Receiver 96 and Chair Handle Receiver 98 attach Chair Handle Belt 32 to the wheelchair handles at the upper rear section of the wheelchair. Torso Belt 28 and Torso Belt 30 interconnect with Chair Handle Belt 32 between the two handles at the upper rear section of the wheelchair back.

Figure 10:
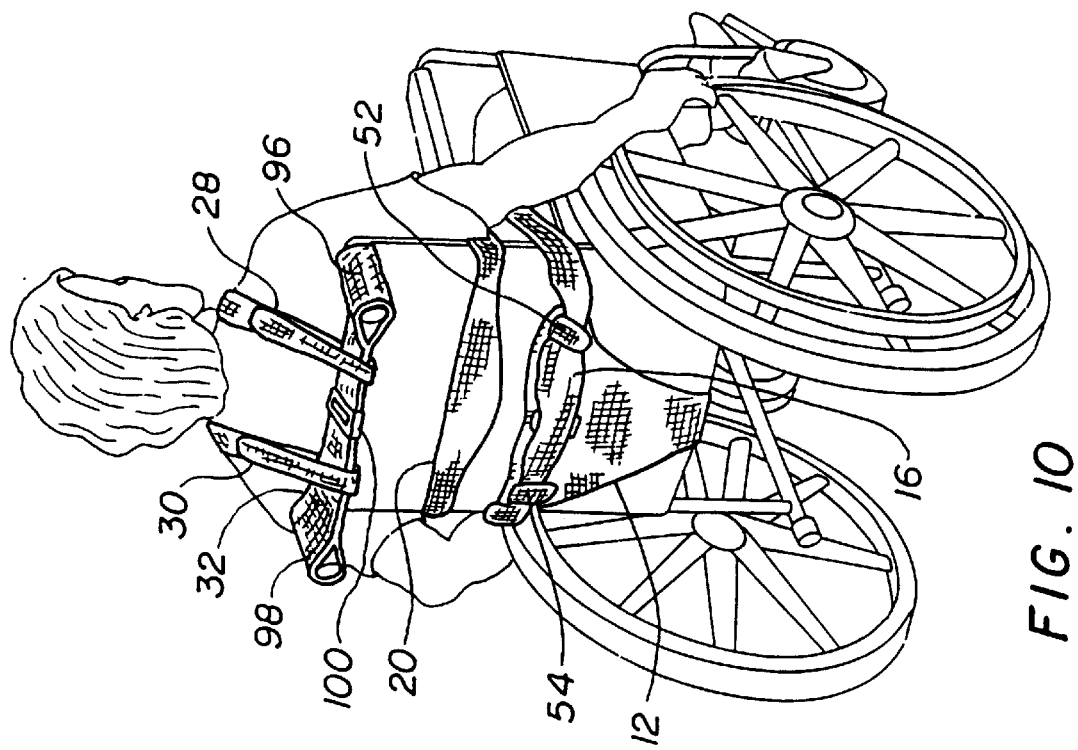
FIG. 10 is a rear view of the belt system as selectively configured in FIG. 9 for providing lower body support and a maximum level of upper body support in a wheelchair.
Figure 9:
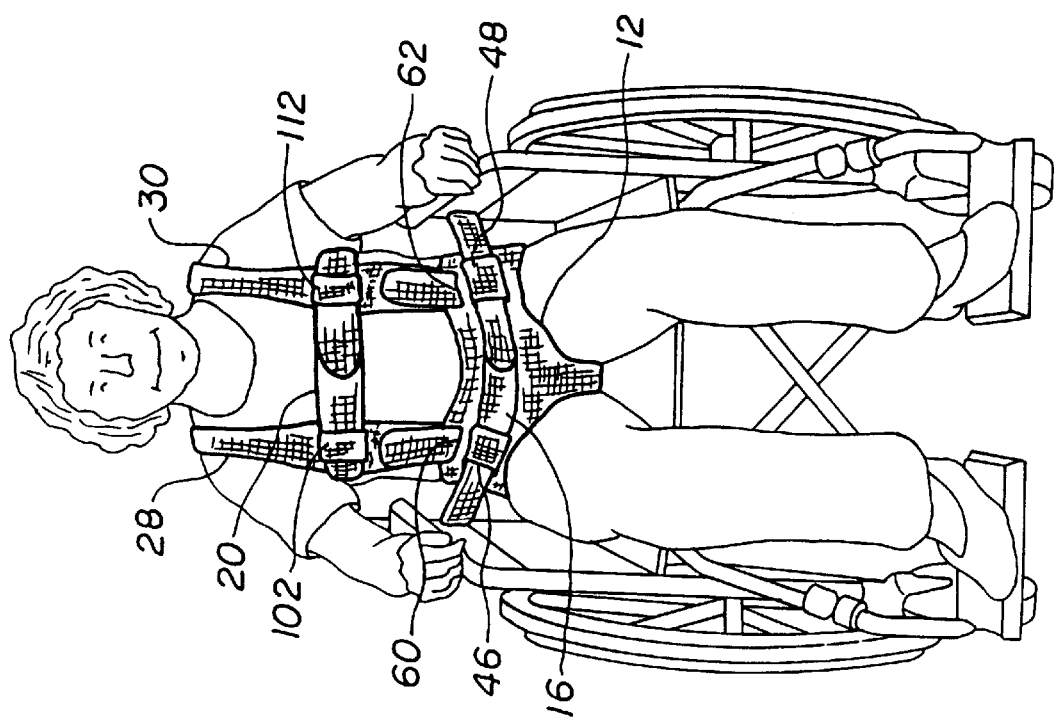
FIG. 9 is a front view of the belt system providing lower body support and a maximum level of upper body support in a wheelchair.

FIG. 9 and FIG. 10 show another of the multiple applications of the inventive adaptive patient restraint and support system. Pelvic Support 12, Chest Belt 20, Torso Belt 28, Torso Belt 30, and Chair Handle Belt 32 can function to control movement of the patient's upper body relative to a wheelchair back in a wheelchair application. Pelvic Support 12 is positioned on the patient by positioning the front section of Pelvic Support 12 along the front of the patient's waist, positioning the center section of Pelvic Support 12 between the patient's legs, and positioning the rear section of Pelvic Support 12 along the rear of the patient's waist. Pelvic Support 12 is secured around the patient's waist by connecting Fastener 38 with Fastener 40 along the right side of the patient's waist area, and by connecting Fastener 42 with Fastener 44 along the left side of the patient's waist area. Torso Belt 28 is positioned along the front right side of the patient's chest, over the patient's right shoulder, over the top of the wheelchair back, and along the rear right section of the wheelchair back. Torso Belt 30 is positioned along the front left of the patient's chest, over the patient's left shoulder, over the top of the wheelchair back, and along the rear left section of the wheelchair back. Torso Belt 28 interconnects with Pelvic Support 12 at the front right waist area of the patient by first passing the first end of Torso Belt 28 through Eyelet 60, and then connecting Fastener 108 with Fastener 110 together to form the interconnection. Torso Belt 30 interconnects with Pelvic Support 12 at the front left waist area of the patient by first passing the first end of Torso Belt 30 through Eyelet 62, and then connecting Fastener 118 with Fastener 120 to form the interconnection. Chair Handle Belt 32 is attached to the two handles at the upper rear section of the wheelchair. Fastener 108 is connected with Fastener 110 to interconnect Torso Belt 28 with Chair Handle Belt 32 between the two handles at the upper rear section of the wheelchair back. Fastener 118 is connected with Fastener 120 to interconnect Torso Belt 30 with Chair Handle Belt 32 between the two handles at the upper rear section of the wheelchair back. Chest Belt 20 is passed through Belt Loop 102 along the front right side of the patient's chest, passed around the rear of the wheelchair back, and passed through Belt Loop 112 along the front left side of the patient's chest. Alternatively, Chest Belt 20 is passed through Belt Loop 102 along the front right side of the patient's chest, passed around the patient's back, and passed through Belt Loop 112 along the front left side of the patient's chest. In either configuration, Fastener 72 is connected with Fastener 74 to complete the interconnection of Chest Belt 20 with Torso Belt 28 and Torso Belt 30. Fastener 72 is connected with Fastener 74 in front of the patient, or otherwise within the patient's reach, such that Pelvic Support 12, Chest Belt 20, Torso Belt 28, Torso Belt 30, and Chair Handle Belt 32 function to provide the patient with a maximum level of upper body support. Alternatively, Fastener 72 is connected with Fastener 74 behind the patient or behind the wheelchair back, or otherwise outside of the patient's reach, such that Pelvic Support 12, Chest Belt 20, Torso Belt 28, Torso Belt 30, and Chair Handle Belt 32 function to provide the patient with a maximum level of upper body restraint (not shown). The maximum level of upper body support or upper body restraint functions to prevent the patient from falling to one side or the other in a wheelchair, to prevent the patient from falling forward in a wheelchair, and to prevent the patient from getting out of a wheelchair seat, and is complemented by the body support or body restraint at the waist, as described above.

Bed Restraint Belt 36 can be interconnected with Pelvic Support 12 to provide the required level of physical restraint while at the same time allowing the patient to experience the optimum freedom of safe movement when the patient is placed in a bed. Bed Restraint Belt 36 includes Eyelet 122 that is located about one-fourth of the way along the length of Bed Restraint Belt 36 and that divides Bed Restraint Belt 36 so as to define a short end and a long end. Bed Restraint Belt 36 also includes Fasteners 124, 126 located at the short end of the belt, and Fasteners 128, 130 located at the long end of the belt. Eyelet 122 is sized to allow the long end of Bed Restraint Belt 36 to be easily passed therethrough for positioning Bed Restraint Belt 36 around a patient. Fasteners 124, 126 and Fasteners 128, 130 are preferred to be fabricated from a hook-and-loop type material to allow the caregiver to easily interconnect Bed Restraint Belt 36 with the bed, and to easily adjust the length of Bed Restraint Belt 36 to conform with various patient sizes. When used in conjunction with Garment System 150, Eyelet 122 is positioned across the lower center area of the patient's back, one end of Bed Restraint Belt 36 is passed around the patient and interconnected with the garment system and passed through Eyelet 122. The two ends of Bed Restraint Belt 36 are secured to opposite sides of the bed frame and outside of the patient's reach by connecting Fasteners 124, 126 together to interconnect the short end of Bed Restraint Belt 36 to one side of the bed frame and by connecting Fasteners 128, 130 together to interconnect the long end of Bed Restraint Belt 36 to the other side of the bed frame.

Bed Restraint Belt 36 is preferred to be made of material which is strong, soft, non-stretchable, and washable, and which can be dyed in various colors and printed with designs and essential information; and which can be made in different sizes and different lengths to satisfy a range of patient sizes. Bed Restraint Belt 36 is used with Pelvic Support 12 to minimize the patient's sensation of being restrained and to maintain the patient's dignity and self-image. In addition, Bed Restraint Belt 36 can function in combination with Garment System 150, and Bed Restraint Belt 36 can function on its own.

Belt System 10 is adjustable and interchangeable and functions to provide both patient support and patient restraint depending upon how the components of Belt System 10 are positioned and fastened in relation to the patient and a chair, a gerichair, or a wheelchair. When Belt System 10 functions as an adaptive and adjustable patient support system, the caregiver fastens Lap Belt 16 and Chest Belt 20 either in front of the patient or otherwise within the patient's reach. Thus, Belt System 10 can function as an adaptive and adjustable patient support system to provide the required level of physical support and safety, while at the same time allowing the patient to easily connect, disconnect, and adjust Lap Belt 16 and Chest Belt 20. Alternatively, when Belt System 10 functions as an adaptive and adjustable patient restraint system, the caregiver fastens Lap Belt 16 and Chest Belt 20 either behind the patient or otherwise outside of the patient's reach. Thus, Belt System 10 can function as an adaptive and adjustable patient restraint system to provide the required level of physical restraint and safety.

Belt System 10 can be configured to provide a minimum level of patient support and restraint, a medium level of patient support and restraint, and a maximum level of patient support and restraint, as required, to satisfy a range of patient medical and safety needs. In applications where either the maximum level of support or restraint is being used or the medium level of support or restraint is being used, and the patient's condition subsequently improves, the adjustability and selectability and flexibility of Belt System 10 allow the caregiver to gradually reduce the level of physical support or physical restraint proportionate to the patient's improvement. Alternatively, in applications where the minimum level of support or restraint is being used or the medium level of support or restraint is being used, and the patient's condition subsequently deteriorates, the adjustability and selectability and flexibility of Belt System 10 allow the caregiver to gradually increase the level of physical support or physical restraint proportionate to the patient's deterioration.

The caregiver can adjust and selectively configure Belt System 10 to satisfy the medical and safety needs of each patient. Belt System 10 solves many common seating and sleeping requirements associated with patients requiring either physical support or physical restraint without necessitating that the caregiver purchase a multitude of single-purpose products or other specialty products. Belt System 10 functions with various chair sizes and types, various gerichair sizes and types, and various wheelchair sizes and types. The components of Belt System 10 can be color-coded to allow the caregiver to easily configure the components to provide the desired level of physical support or physical restraint.

Garment System 150 can be used in combination with Belt System 10 to provide the level of physical support and physical restraint necessary to satisfy a patient's medical and safety needs while at the same time providing such support and restraint discreetly so as to enhance the patient's self-image. Garment System 150 complements Belt System 10 to provide the necessary patient support and restraint while minimizing self-image deflating stigmas associated with visible support and restraint devices (e.g., belts, vests, jackets) that draw attention to the patient's physical disability or mental impairment. Garment System 150 and Belt System 10 are used in combination to provide adaptive support and restraint which can be selectively configured and adjusted by the caregiver to satisfy a patient's medical and safety needs when the patient is seated in a chair, a gerichair, or a wheelchair, or when the patient is lying or sitting in a bed. Garment System 150 functions to distribute the stresses associated with physically supporting a patient or physically restraining a patient over a broad area of the body to allow increased ranges of patient control with decreased risk of injury or skin irritation for the patient.

Figure 11B:
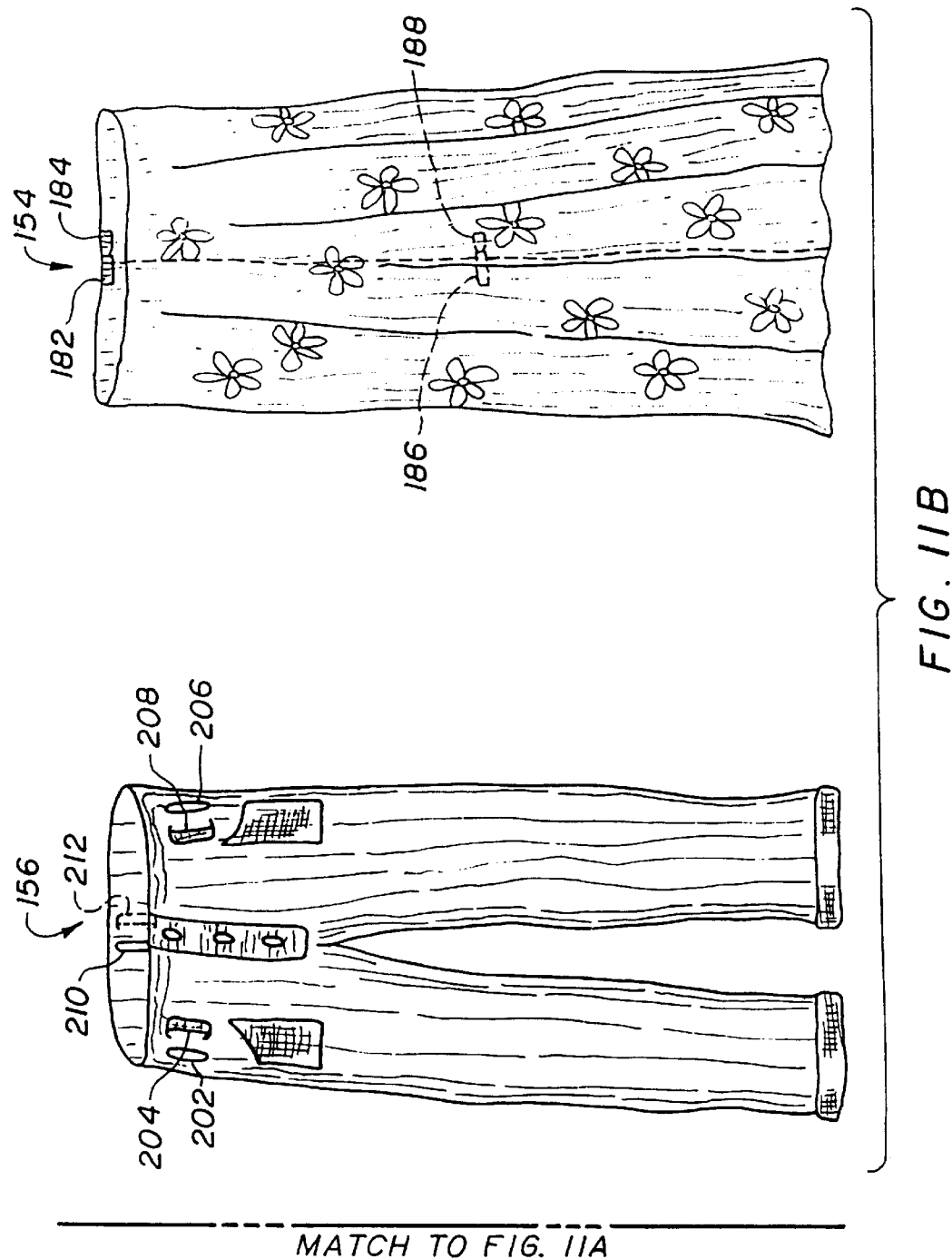

FIG. 11A and FIG. 11B, taken together, illustrate the components of Garment System 150 that function in combination with Belt System 10 for providing adaptive patient support and restraint, and function in combination with Belt System 10 and Seating Cushion System 250, discussed below, for providing adaptive patient support and restraint. Garment System 150 includes Body Suit 152, Lap Robe 154, Pant 156, and Shirt 158. In addition to functioning for providing adaptive patient support and restraint, Body Suit 152, Lap Robe 154, Pant 156, and Shirt 158 further function as clothing, with Pant 156 and Shirt 158 still further functioning as pajamas. As described herein, the term "pant" refers to a pair of trousers, a pair of pants, or a pair of slacks, i.e., a garment for substantially covering the body from the waist to the ankles which is divided into sections to fit each leg separately. As described herein, the term "shirt" refers to a shirt or a blouse, i.e., a garment for substantially covering the body from the neck to the waist which includes a collar and sleeves.

The garments of Garment System 150 can be configured for use by either female patients, male patients, or both female patients and male patients. Further, the garments of Garment System 150 can be sized having dimensions selected for use by either female patients, male patients, or both female patients and male patients. Body Suit 152, Lap Robe 154, Pant 156, and Shirt 158 are preferred to be made of materials which are soft, stretchable, washable, breathable, and which have sufficient strength to function both as patient support devices and as patient restraint devices. In addition, the components of Garment System 150 are preferred to be of materials having a variety of colors and patterns to provide the patient with a wardrobe that, while serving a medical or safety function, is also colorful and fashionable to enhance the patient's self-image.

Referring to FIG. 11A, Body Suit 152 includes integral Flap 160 extending from the rear waist section of Body Suit 152. Flap 160 is configured to easily pass between a patient's legs for positioning along the front waist area of the patient. Body Suit 152, including Flap 160, functions both as a garment and as a pelvic support device. Body Suit 152 includes Belt Loop 162 along the front right waist section, Belt Loop 164 along the front left waist section, Belt Loop 166 on Flap 160, Belt Loop 168 along the rear right shoulder section, Belt Loop 170 along the rear left shoulder section, Belt Loop 172 along the rear center shoulder section, and Belt Loop 174 along the rear center waist section. Body Suit 152 includes Fastener 176 along the front right waist section and Fastener 177 along the front left waist section, and Flap 160 of Body Suit 152 includes Fastener 178 along the right waist section and Fastener 179 along the left waist section. Fastener 176 is connected with Fastener 178 for securing Flap 160 with the front right waist section of Body Suit 152, and Fastener 177 is connected with Fastener 179 for securing Flap 160 with the front left section of Body Suit 152. Fasteners such as hook-type fasteners and loop-type fasteners can be used as the complementary fastener pair of Fasteners 176, 178 and the complementary fastener pair of Fasteners 177, 179 to allow the caregiver to easily connect Flap 160 with the front of Body Suit 152, to easily disconnect Flap 160 from the front of Body Suit 152, and to easily adjust Body Suit 152 for different patient sizes. However, it is contemplated that fasteners other than hook-type fasteners and loop-type fasteners can be used for connecting Flap 160 of Body Suit 152 with the front waist section of Body Suit 152. Any type of fastener can be used for connecting Flap 160 of Body Suit 152 with the front waist section of Body Suit 152, and the invention is not specifically not limited to the representative hook-type fasteners and loop-type fasteners as shown in FIG. 11A. It is to be appreciated that while Fastener 176 and Fastener 178 must be able to connect with one another and Fastener 177 must be able to connect with Fastener 179, there is no requirement that Fastener 176 must be one type of fastener (e.g., a hook-type fastener) and that Fastener 178 must be the other type of fastener (e.g., the loop-type fastener), nor is there a requirement that Fastener 177 must be one type of fastener (e.g., a hook-type fastener) and that Fastener 179 must be the other type of fastener (e.g., the loop-type fastener). For example, as shown in FIG. 11A for Body Suit 152, Fastener 176 can be a hook-type fastener and Fastener 178 can be a loop-type fastener, or, alternatively, Fastener 176 can be a loop-type fastener and Fastener 178 can be a hook-type fastener. By further example, Fastener 177 can be a hook-type fastener and Fastener 179 can be a loop-type fastener, or, alternatively, Fastener 177 can be a loop-type fastener and Fastener 179 can be a hook-type fastener. It is to be further appreciated that while the Fasteners 176, 178 are shown providing a limited range of adjustability, a greater range of adjustability is contemplated by, for example, using a long strip of hook-type material for one of the fasteners, using a long strip of a loop-type material for one of the fasteners, or using both a long strip of a hook-type material for one of the fasteners and a long strip of a loop-type material for the other of the fasteners. It is to be still further appreciated that while the Fasteners 177, 179 are shown providing a limited range of adjustability, a greater range of adjustability is contemplated by, for example, using a long strip of hook-type material for one of the fasteners, using a long strip of a loop-type material for one of the fasteners, or using both a long strip of a hook-type material for one of the fasteners and a long strip of a loop-type material for the other of the fasteners. It is to be still further appreciated that Body Suit 152 can be made in various sizes of jump suits and thereby eliminate Fasteners 176, 178 and Fasteners 177, 179 from Body Suit 152.

Figure 13:
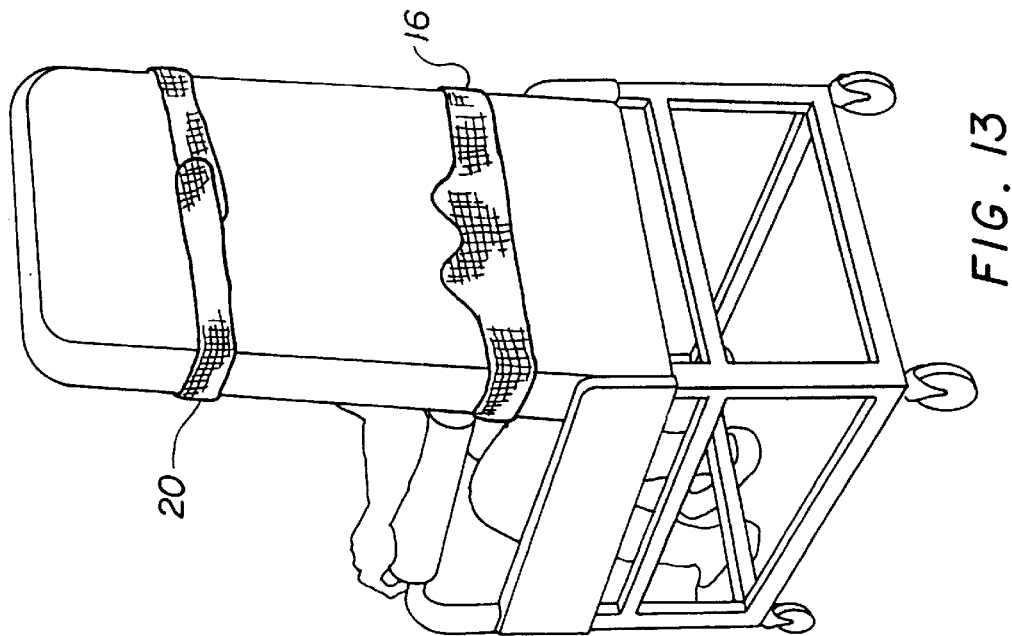
FIG. 13 is a rear view of the body suit as selectively configured in FIG. 12 being used in combination with the belt system for providing lower body support and upper body restraint in a gerichair.
Figure 12:
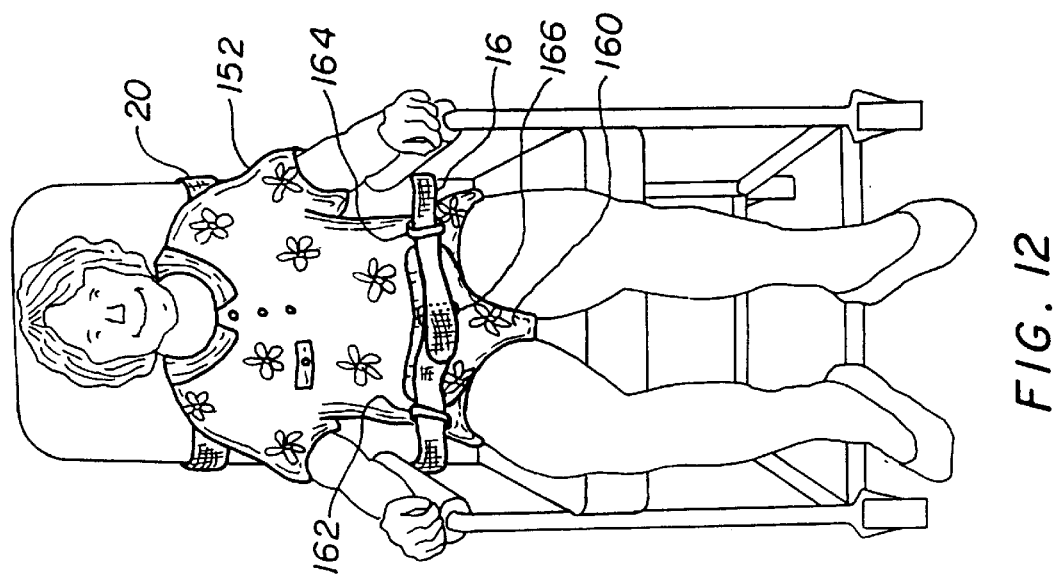
FIG. 12 is a front view of the body suit being used in combination with the belt system for providing lower body support and upper body restraint in a gerichair.

FIG. 12 and FIG. 13 show another of the multiple applications of the inventive adaptive patient restraint and support system. Body Suit 152, Lap Belt 16, and Chest Belt 20 can function to provide total body restraint in a gerichair application, and to provide total body support in a gerichair application. Body Suit 152 is positioned on the patient with Flap 160 being positioned between the patient's legs and along the patient's front waist area. Fastener 176 is connected with Fastener 178 to secure Flap 160 with the front right waist section of Body Suit 152, and Fastener 177 is connected with Fastener 179 to secure Flap 160 with the front left waist section of Body Suit 152. To prevent the patient from sliding out of the gerichair in a support mode, Lap Belt 16 is passed through Belt Loops 162, 164 along the front waist area of the patient and is also passed along the rear of the gerichair back. To prevent the patient from sliding out of the gerichair in a restraint mode, Lap Belt 16 is passed through Belt Loops 162, 164, 166 along the front waist area of the patient and is also passed along the rear of the gerichair back (not shown). If additional body control is required, Pelvic Support Belt 14 can be positioned through Belt Loop 174 at the rear center waist section of Body Suit 152 and Lap Belt 16 can also be passed through D-Rings 56, 58 along the sides of the patient. Fastener 64 is connected with Fastener 66 to secure Lap Belt 16. Fastener 64 can be connected with Fastener 66 in front of the patient, or otherwise within the patient's reach, such that the combination of Lap Belt 16 and Body Suit 152 functions to physically support the patient's body. Alternatively, Fastener 64 can be connected with Fastener 66 behind the gerichair back, or otherwise outside of the patient's reach, such that the combination of Lap Belt 16 and Body Suit 152 functions to physically restrain the patient's body (not shown). For controlling movement of the patient's upper body, Chest Belt 20 is passed through Belt Loop 172 at the patient's rear center shoulder area and is passed along the rear of the gerichair back. Fastener 72 is connected with Fastener 74 to secure Chest Belt 20, such that the combination of Chest Belt 20 and Body Suit 152 functions to physically restrain the patient's body.

Figure 15:
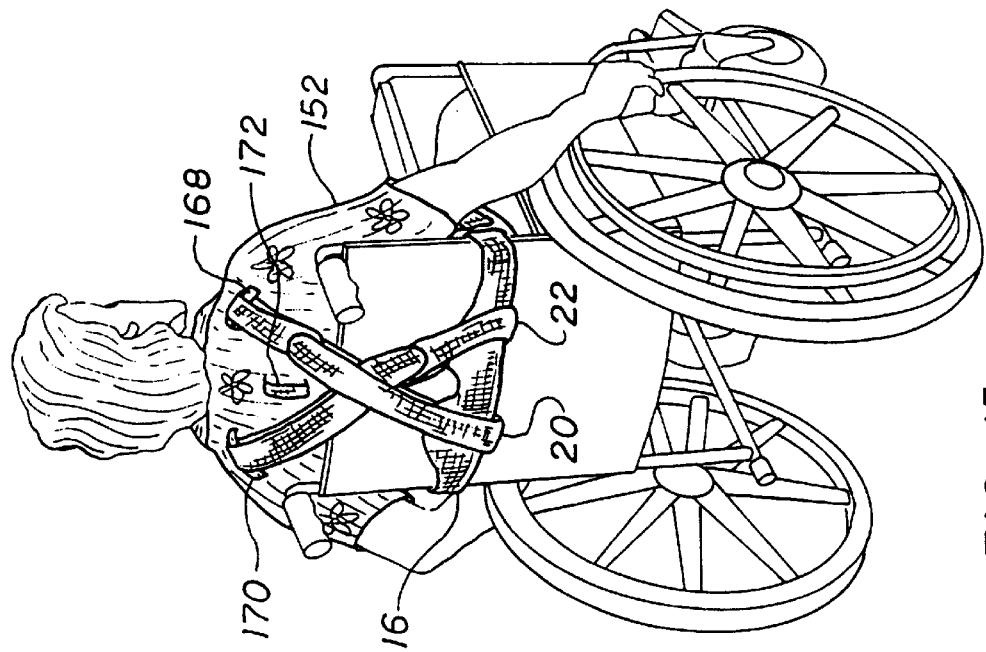
FIG. 15 is a rear view of the body suit as selectively configured in FIG. 14 being used in combination with the belt system for providing lower body support and upper body restraint in a wheelchair.
Figure 14:
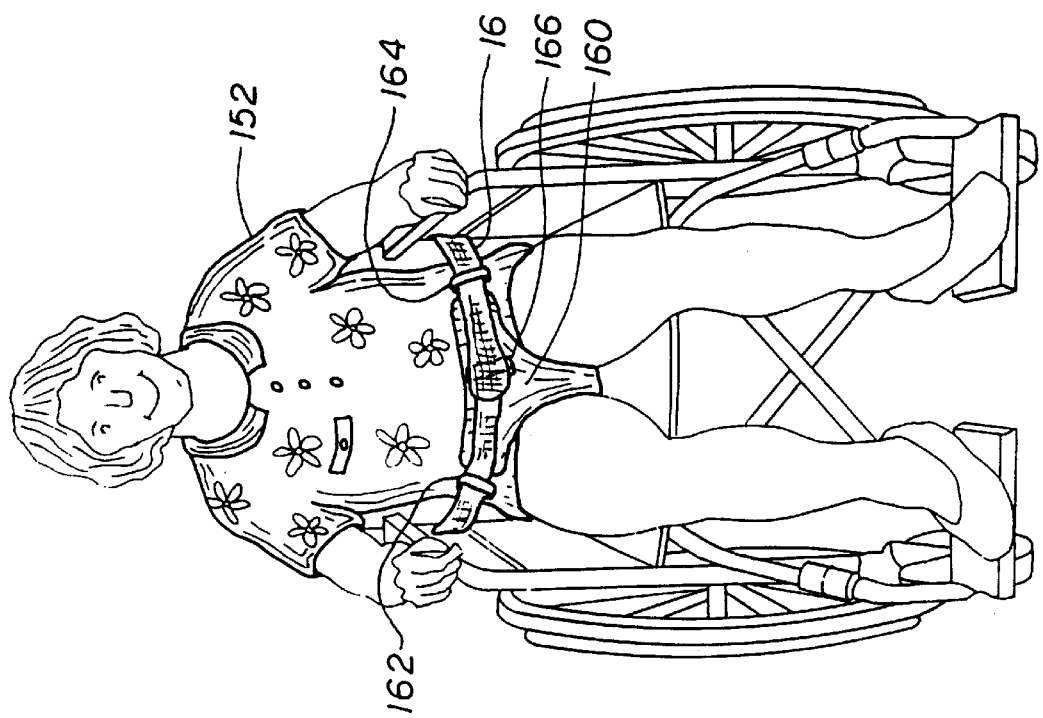
FIG. 14 is a front view of the body suit being used in combination with the belt system for providing lower body support in a wheelchair.

FIG. 14 and FIG. 15 show another of the multiple applications of the inventive adaptive patient restraint and support system. Body Suit 152, Lap Belt 16, Chest Belt 20, and Chest Belt 22 can function to provide upper body restraint in a wheelchair application, and to provide either body support or body restraint at the waist in a wheelchair application. Body Suit 152 is positioned on the patient with Flap 160 being positioned between the patient's legs and along the patient's front waist area. Fastener 176 is connected with Fastener 178 to secure Flap 160 with the front right waist section of Body Suit 152, and Fastener 177 is connected with Fastener 179 to secure Flap 160 with the front left waist section of Body Suit 152. To prevent the patient from sliding out of the wheelchair in a support mode, Lap Belt 16 is passed through Belt Loops 162, 164 along the front waist area of the patient and is also passed along the rear of the wheelchair back. To prevent the patient from sliding out of the wheelchair in a restraint mode, Lap Belt 16 is passed through Belt Loops 162, 164, 166 along the front waist area of the patient and is also passed along the rear of the wheelchair back (not shown). If additional body control is required, Pelvic Support Belt 14 can be positioned through Belt Loop 174 at the rear center waist section of Body Suit 152 and Lap Belt 16 can also be passed through D-Rings 56, 58 along the sides of the patient. Fastener 64 is connected with Fastener 66 to secure Lap Belt 16. Fastener 64 can be connected with Fastener 66 in front of the patient, or otherwise within the patient's reach, such that the combination of Lap Belt 16 and Body Suit 152 functions to physically support the patient's body at the waist. Alternatively, Fastener 64 can be connected with Fastener 66 behind the wheelchair back, or otherwise outside of the patient's reach, such that the combination of Lap Belt 16 and Body Suit 152 functions to physically restrain the patient's body at the waist (not shown). For controlling movement of the patient's right upper body, Chest Belt 20 is passed through Belt Loop 168 at the patient's rear right shoulder area and is passed around Lap Belt 16 at the rear left section of the wheelchair back. Fastener 72 is connected with Fastener 64 to secure Chest Belt 20, such that the combination of Lap Belt 16, Chest Belt 20, and Body Suit 152 functions to physically restrain the patient's upper body. For controlling movement of the patient's left upper body, Chest Belt 22 is passed through Belt Loop 170 at the patient's rear left shoulder area and is passed around Lap Belt 16 at the rear right section of the wheelchair back. Fastener 76 is connected with Fastener 78 to secure Chest Belt 22, such that the combination of Lap Belt 16, Chest Belt 22, and Body Suit 152 functions to physically restrain the patient's upper body.

Body Suit 152 is configured to permit the caregiver to easily pull the garment over the patient's head for dressing and undressing the patient. Fasteners 176, 178 and Fasteners 177, 179 allow the caregiver to secure Flap 160 along the front waist section of Body Suit 152 so as to allow Lap Belt 16 to be easily passed through Belt Loops 162, 164, 166 along the front waist area of the patient. By configuring Flap 160 to open at the front waist area of a patient, the caregiver can easily open Flap 160 away from a patient's waist in a dignified manner so as to provide immediate care for an incontinent patient or a patient requiring other assistance. It is to be appreciated that Body Suit 152 can include a series of snaps, buttons, or other connecting means on the front of the garment to permit the caregiver to open Body Suit 152 for easy positioning of the garment on the patient, and for easy removal of the garment from the patient, without necessitating pulling Body Suit 152 over the patient's head.

Figure 16:
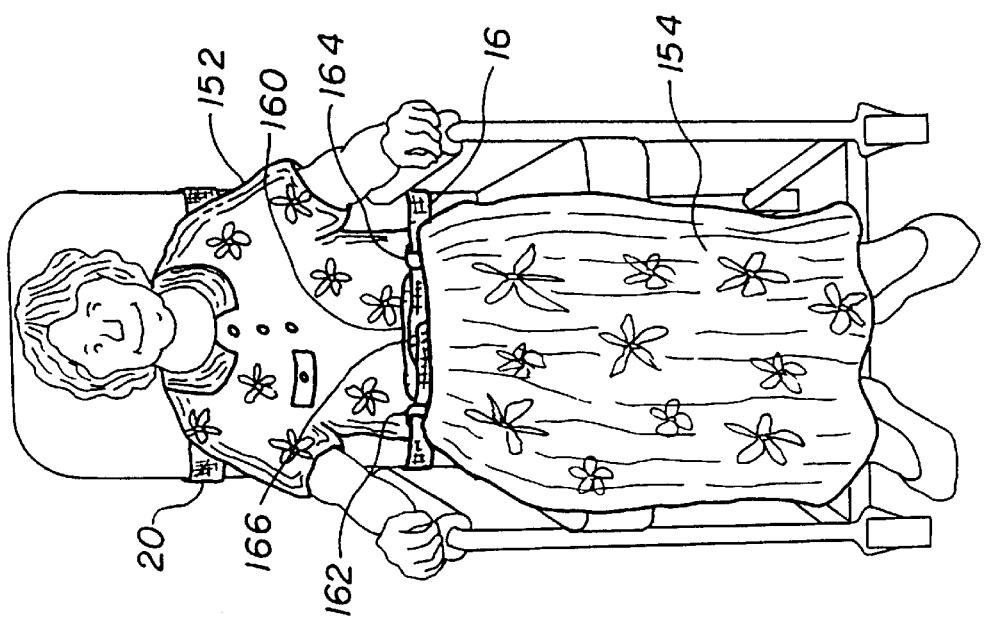
FIG. 16 is a front view of the body suit and the lap robe being used in combination with the belt system for providing lower body support and upper body restraint in a gerichair.

FIG. 16 shows another of the multiple applications of the inventive adaptive patient restraint and support system. Lap Robe 154 can function in combination with Body Suit 152 to provide a wrap-around modesty garment to cover a patient's lower body and legs in multiple applications. Lap Robe 154 includes Fasteners 182, 184 along the waist section and Fasteners 186, 188 along the knee section. Fasteners 182, 184 and Fasteners 186, 188 are preferred to be fabricated from a hook-and-loop type material to allow the caregiver to easily position Lap Robe 154 around the patient, and to easily adjust Lap Robe 154 for different patient sizes. Lap Robe 154 is positioned around the patient's waist area and around the patient's legs. Fastener 182 is connected with Fastener 184 at the patient's waist area, and Fastener 186 is connected with Fastener 188 at the patient's knee area.

Lap Robe 154 functions in a chair application, a gerichair application, and a wheelchair application. Lap Robe 154 permits the patient to retain body heat so as to maintain the patient's lower body and legs at a comfortable level of warmth and to cover exposed areas of the patient's body. In addition, Lap Robe 154 is configured to permit the caregiver to quickly remove Lap Robe 154 to provide immediate care for an incontinent patient or a patient requiring other assistance, and to permit the caregiver to quickly access components that can be positioned under Lap Robe 154, including Lap Belt 16, Pelvic Support 12, Pelvic Support Belt 14, and Body Suit 152.

Pant 156 and Shirt 158 function in combination with Belt System 10. Referring to FIG. 11B, Pant 156 includes Eyelet 202 and Belt Loop 204 at the front right waist section, Eyelet 206 and Belt Loop 208 at the front left waist section, and Eyelet 210 and Belt Loop 212 at the rear center waist section. Referring to FIG. 11A, Shirt 158 includes Belt Loop 222 and Eyelet 224 at the front right waist section, Belt Loop 226 and Eyelet 228 at the front left waist section, Belt Loop 230 and Eyelet 232 at the rear center waist section, Belt Loop 234 at the rear right shoulder section, Belt Loop 236 at the rear left shoulder section, and Belt Loop 238 at the rear center shoulder section.

Pant 156 and Lap Belt 16 can be used in a chair application, a gerichair application, or a wheelchair application to provide either body support or body restraint. Pant 156 is positioned on the patient. For controlling movement of the patient's body, Lap Belt 16 is passed through Belt Loops 204, 208 along the front waist area of the patient and is also passed along either the rear of a chair back, the rear of a gerichair back or the rear of a wheelchair back. If additional body control is required, Pelvic Support Belt 14 can be positioned through Belt Loop 212 at the rear center waist section of Pant 156, and Lap Belt 16 can also be passed through D-Rings 56, 58 along the sides of the patient. Fastener 64 is connected with Fastener 66 to secure Lap Belt 16. Fastener 64 can be connected with Fastener 66 in front of the patient, or otherwise within the patient's reach, such that the combination of Lap Belt 16 and Pant 156 functions to physically support the patient's body at the waist. Alternatively, Fastener 64 can be connected with Fastener 66 behind either the chair back, the gerichair back, or the wheelchair back, or otherwise outside of the patient's reach, such that the combination of Lap Belt 16 and Pant 156 functions to physically restrain the patient's body at the waist.

Body Suit 152, Pant 156, Lap Belt 16, and Chest Belt 20 can be used in a gerichair application to provide upper body restraint, and to provide either body support or body restraint at the waist. Body Suit 152 is positioned on the patient with Flap 160 being positioned between the patient's legs and along the front of the patient's waist area. Fastener 176 is connected with Fastener 178 to secure Flap 160 with the front right waist section of Body Suit 152, and Fastener 177 is connected with Fastener 179 to secure Flap 160 with the front left waist section of Body Suit 152. Pant 156 is positioned on the patient with the waist section of Pant 156 being positioned over the waist section of Body Suit 152. Belt Loop 162 is positioned through Eyelet 202 along the front right waist area of the patient and Belt Loop 164 is positioned through Eyelet 206 along the front left waist area of the patient. For controlling movement of the patient's body at the waist, Lap Belt 16 is passed through Belt Loops 162, 164 along the front waist area of the patient and is also passed along the rear of the gerichair back. If additional body control is required, Pelvic Support Belt 14 can be positioned through Belt Loop 174 at the rear center waist section of Body Suit 152 and Lap Belt 16 can also be passed through D-Rings 56, 58 along the sides of the patient. Fastener 64 is connected with Fastener 66 to secure Lap Belt 16. Fastener 64 can be connected with Fastener 66 in front of the patient, or otherwise within the patient's reach, such that the combination of Lap Belt 16, Body Suit 152, and Pant 156 functions to physically support the patient's body at the waist. Alternatively, Fastener 64 can be connected with Fastener 66 behind the gerichair back, or otherwise outside of the patient's reach, such that the combination of Lap Belt 16, Body Suit 152, and Pant 156 function to physically restrain the patient's body at the waist. For controlling movement of the patient's upper body, Chest Belt 20 is passed through Belt Loop 172 at the patient's rear center shoulder area and is passed along the rear section of the gerichair back. Fastener 72 is connected with Fastener 74 to secure Chest Belt 20, such that the combination of Chest Belt 20 and Body Suit 152 functions to physically restrain the patient's upper body.

Figure 17:
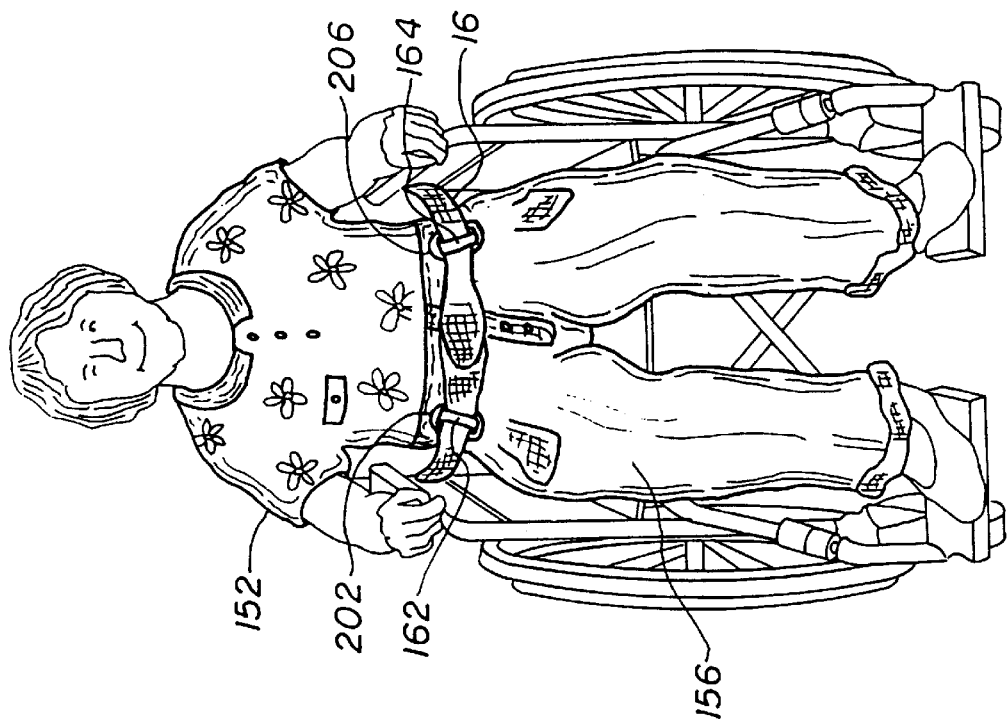
FIG. 17 is a front view of the body suit and the pant being used in combination with the belt system for providing lower body support in a wheelchair.

FIG. 17 shows another of the multiple applications of the inventive adaptive patient restraint and support system. Body Suit 152, Pant 156, Lap Belt 16, Chest Belt 20, and Chest Belt 22 can function to provide upper body restraint in a wheelchair application, and to provide either body support or body restraint at the waist in a wheelchair application. Body Suit 152 is positioned on the patient with Flap 160 being positioned between the patient's legs and along the front of the patient's waist area. Fastener 176 is connected with Fastener 178 to secure Flap 160 with the front right waist section of Body Suit 152, and Fastener 177 is connected with Fastener 179 to secure Flap 160 with the front left waist section of Body Suit 152. Pant 156 is positioned on the patient with the waist section of Pant 156 being positioned over the waist section of Body Suit 152. Belt Loop 162 is positioned through Eyelet 202 along the front right waist area of the patient and Belt Loop 164 is positioned through Eyelet 206 along the front left waist area of the patient. For controlling movement of the patient's body, Lap Belt 16 is passed through Belt Loops 162, 164 along the front waist area of the patient and is also passed along the rear of the wheelchair back. If additional body control is required at the waist, Belt Loop 174 can be positioned through Eyelet 210 along the rear center waist area of the patient, Pelvic Support Belt 14 can be positioned through Belt Loop 174 at the rear center waist section of Body Suit 152, and Lap Belt 16 can also be passed through D-Rings 56, 58 along the sides of the patient. Fastener 64 is connected with Fastener 66 to secure Lap Belt 16. Fastener 64 can be connected with Fastener 66 in front of the patient, or otherwise within the patient's reach, such that the combination of Lap Belt 16, Body Suit 152, and Pant 156 functions to physically support the patient's body at the waist. Alternatively, Fastener 64 can be connected with Fastener 66 behind the wheelchair back, or otherwise outside of the patient's reach, such that the combination of Lap Belt 16, Body Suit 152, and Pant 156 functions to physically restrain the patient's body at the waist (not shown). For controlling movement of the patient's right upper body, Chest Belt 20 is passed through Belt Loop 168 at the patient's rear right shoulder area and is also passed around Lap Belt 16 at the rear left section of the wheelchair back. Fastener 72 is connected with Fastener 64 to secure Chest Belt 20, such that the combination of Lap Belt 16, Chest Belt 20, and Body Suit 152 functions to physically restrain the patient's upper body. For controlling movement of the patient's left upper body, Chest Belt 22 is passed through Belt Loop 170 at the patient's rear left shoulder area and is also passed around Lap Belt 16 at the rear right section of the wheelchair back. Fastener 76 is connected with Fastener 78 to secure Chest Belt 22, such that the combination of Lap Belt 16, Chest Belt 22, and Body Suit 152 functions to physically restrain the patient's upper body.

Figure 18:
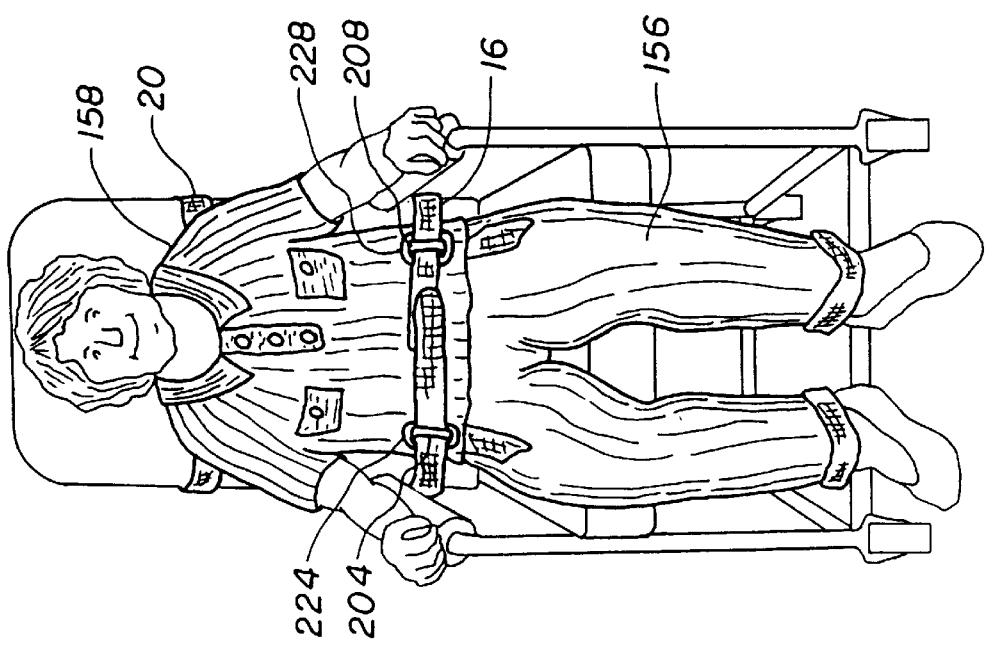
FIG. 18 is a front view of the pant and the shirt being used in combination with the belt system for providing lower body support and upper body restraint in a gerichair.

FIG. 18 shows another of the multiple applications of the inventive adaptive patient restraint and support system. Pant 156, Shirt 158, Lap Belt 16, and Chest Belt 20 can function to provide upper body restraint in a gerichair application, and to provide either body support or body restraint at the waist in a gerichair application. In a first configuration, Pant 156 and Shirt 158 are positioned on the patient with the waist section of Shirt 158 being positioned over the waist section of Pant 156. Belt Loop 204 is positioned through Eyelet 224 along the front right waist area of the patient and Belt Loop 208 is positioned through Eyelet 228 along the front left waist area of the patient. For preventing the patient from sliding down and out of the gerichair in the first configuration, Lap Belt 16 is passed through Belt Loops 204, 208 along the front waist area of the patient and is also passed along the rear of the gerichair back. If additional body control is required at the waist in the first configuration, Belt Loop 212 can be positioned through Eyelet 232 along the rear center waist area of the patient, Pelvic Support Belt 14 can be positioned through Belt Loop 212 at the rear center waist section of Pant 156, and Lap Belt 16 can also be passed through D-Rings 56, 58 along the sides of the patient. In a second configuration, Pant 156 and Shirt 158 are positioned on the patient with the waist section of Pant 156 being positioned over the waist section of Shirt 158 (not shown). Belt Loop 222 is positioned through Eyelet 202 along the front right waist area of the patient and Belt Loop 226 is positioned through Eyelet 206 along the front left waist area of the patient. For preventing the patient from sliding down and out of the gerichair in the second configuration, Lap Belt 16 is passed through Belt Loops 222, 226 along the front waist area of the patient and is also passed along the rear of the gerichair back. If additional body control is required at the waist in the second configuration, Belt Loop 230 can be positioned through Eyelet 210 along the rear center waist area of the patient, Pelvic Support Belt 14 can be positioned through Belt Loop 230 at the rear center waist section of Shirt 158, and Lap Belt 16 can also be passed through D-Rings 56, 58 along the sides of the patient. Fastener 64 is connected with Fastener 66 to secure Lap Belt 16. Fastener 64 can be connected with Fastener 66 in front of the patient, or otherwise within the patient's reach, such that the combination of Lap Belt 16, Pant 156, and Shirt 158 functions to physically support the patient's body at the waist. Alternatively, Fastener 64 can be connected with Fastener 66 behind the gerichair back, or otherwise outside of the patient's reach, such that the combination of Lap Belt 16, Pant 156, and Shirt 158 functions to physically restrain the patient's body at the waist (not shown). For controlling movement of the patient's upper body, Chest Belt 20 is passed through Belt Loop 238 at the patient's rear center shoulder area and is passed along the rear section of the gerichair back. Fastener 72 is connected with Fastener 74 to secure Chest Belt 20, such that the combination of Chest Belt 20 and Shirt 158 functions to physically restrain the patient's upper body.

Figure 19:
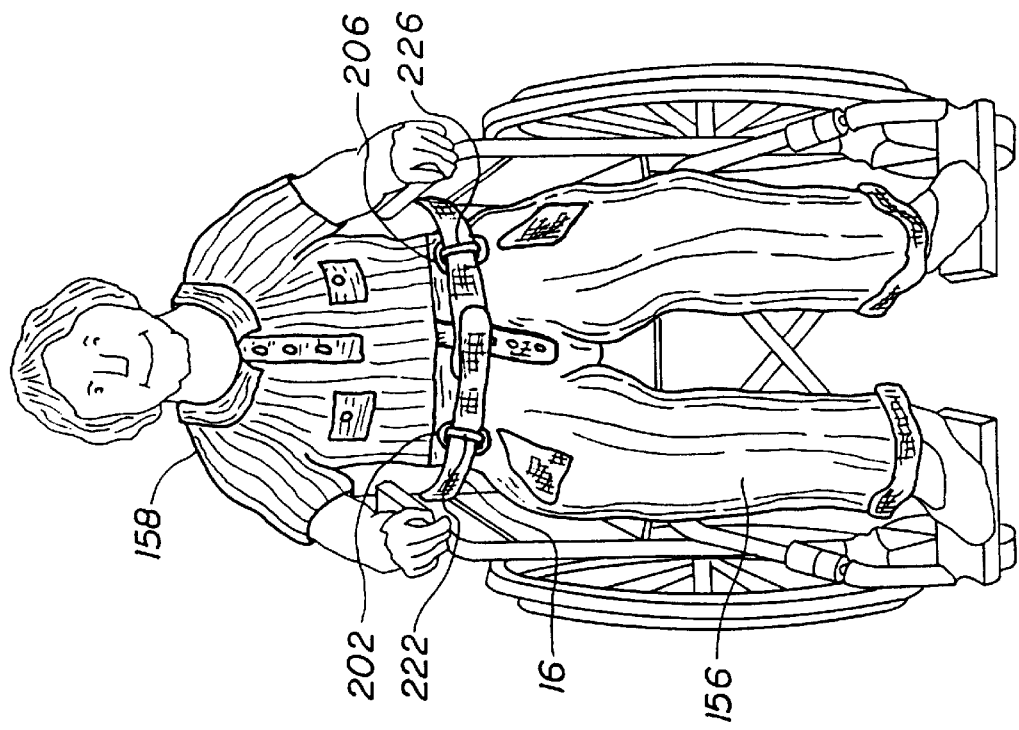
FIG. 19 is a front view of the pant and the shirt being used in combination with the belt system for providing lower body support in a wheelchair.
Figure 20:
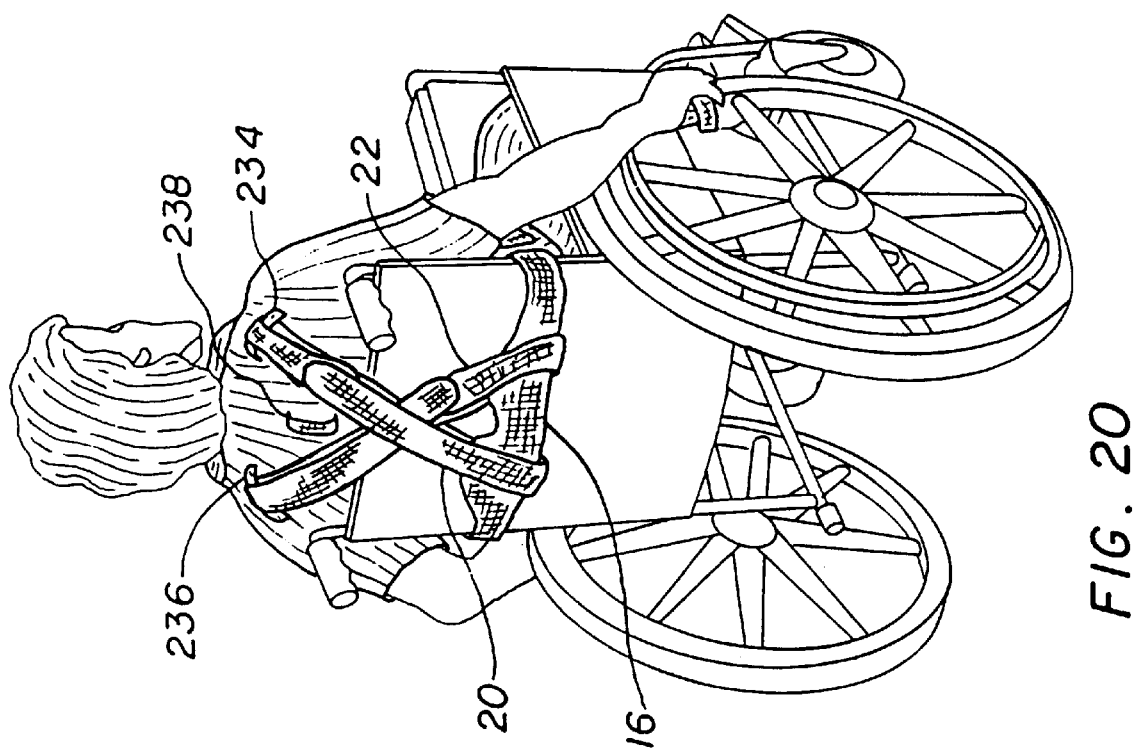
FIG. 20 is a rear view of the pant and the shirt as selectively configured in FIG. 19 being used in combination with the belt system for providing lower body support and upper body restraint in a wheelchair.

FIG. 19 and FIG. 20 show another of the multiple applications of the inventive adaptive patient restraint and support system. Pant 156, Shirt 158, Lap Belt 16, Chest Belt 20, and Chest Belt 22 can function to provide upper body restraint in a wheelchair application, and to provide either body support or body restraint at the waist in a wheelchair application. In a first configuration, Pant 156 and Shirt 158 are positioned on the patient with the waist section of Shirt 158 being positioned over the waist section of Pant 156. Belt Loop 204 is positioned through Eyelet 224 along the front right waist area of the patient and Belt Loop 208 is positioned through Eyelet 228 along the front left waist area of the patient. For controlling movement of the patient's lower body in the first configuration, Lap Belt 16 is passed through Belt Loops 204, 208 along the front waist area of the patient and is passed along the rear of the wheelchair back. If additional body control is required at the waist in the first configuration, Belt Loop 212 can be positioned through Eyelet 232 along the rear center waist area of the patient, Pelvic Support Belt 14 can be positioned through Belt Loop 212 at the rear center waist section of Pant 156, and Lap Belt 16 can also be passed through D-Rings 56, 58 along the sides of the patient. In a second configuration, Pant 156 and Shirt 158 are positioned on the patient with the waist section of Pant 156 being positioned over the waist section of Shirt 158. Belt Loop 222 is positioned through Eyelet 202 along the front right waist area of the patient and Belt Loop 226 is positioned through Eyelet 206 along the front left waist area of the patient. For controlling movement of the patient's body at the waist, Lap Belt 16 is passed through Belt Loops 222, 226 along the front waist area of the patient and is passed along the rear of the wheelchair back. If additional body control is required at the waist in the second configuration, Belt Loop 230 can be positioned through Eyelet 210 along the rear center waist area of the patient, Pelvic Support Belt 14 can be positioned through Belt Loop 230 at the rear center waist section of Shirt 158, and Lap Belt 16 can also be passed through D-Rings 56, 58 along the sides of the patient. Fastener 64 is connected with Fastener 66 to secure Lap Belt 16. Fastener 64 can be connected with Fastener 66 in front of the patient, or otherwise within the patient's reach, such that the combination of Lap Belt 16, Pant 156, and Shirt 158 functions to physically support the patient's body at the waist. Alternatively, Fastener 64 can be connected with Fastener 66 behind the wheelchair back, or otherwise outside of the patient's reach, such that the combination of Lap Belt 16, Pant 156, and Shirt 158 functions to physically restrain the patient's body (not shown). For controlling movement of the patient's right upper body, Chest Belt 20 is passed through Belt Loop 234 at the patient's rear right shoulder area and is passed around Lap Belt 16 at the rear left section of the wheelchair back. Fastener 72 is connected with Fastener 64 to secure Chest Belt 20 such that the combination of Lap Belt 16, Chest Belt 20, and Shirt 158 functions to physically restrain the patient's upper body. For controlling movement of the patient's left upper body, Chest Belt 22 is passed through Belt Loop 236 at the patient's rear left shoulder area and is passed around Lap Belt 16 at the rear right section of the wheelchair back. Fastener 76 is connected with Fastener 78 to secure Chest Belt 22, such that the combination of Lap Belt 16, Chest Belt 22, Shirt 158 function to physically restrain the patient's upper body.

Bed Restraint Belt 36 functions in combination with Garment System 150, or with Pelvic Support 12 and Garment System 150, to comfortably control the movement of a patient in a bed while simultaneously permitting the patient to experience the optimum freedom of movement in the bed. Bed Restraint Belt 36 cooperates with Pelvic Support 12 and Shirt 158, with Pant 156 and Shirt 158, with Body Suit 152, or with Body Suit 152 and Pant 156 to distribute the stresses associated with restraining a patient over a large area of the patient's body to avoid the discomfort and confinement problems encountered with prior bed restraint systems. Bed Restraint Belt 36 is preferred to be made of flexible, stretch-resistant material to comfortably restrain the patient's movement in a bed, to prevent the patient from leaving the bed, to permit the patient to roll from side to side in the bed, and to permit the patient to sit up in the bed, while minimizing the patient's risk of injury.

Figure 21:
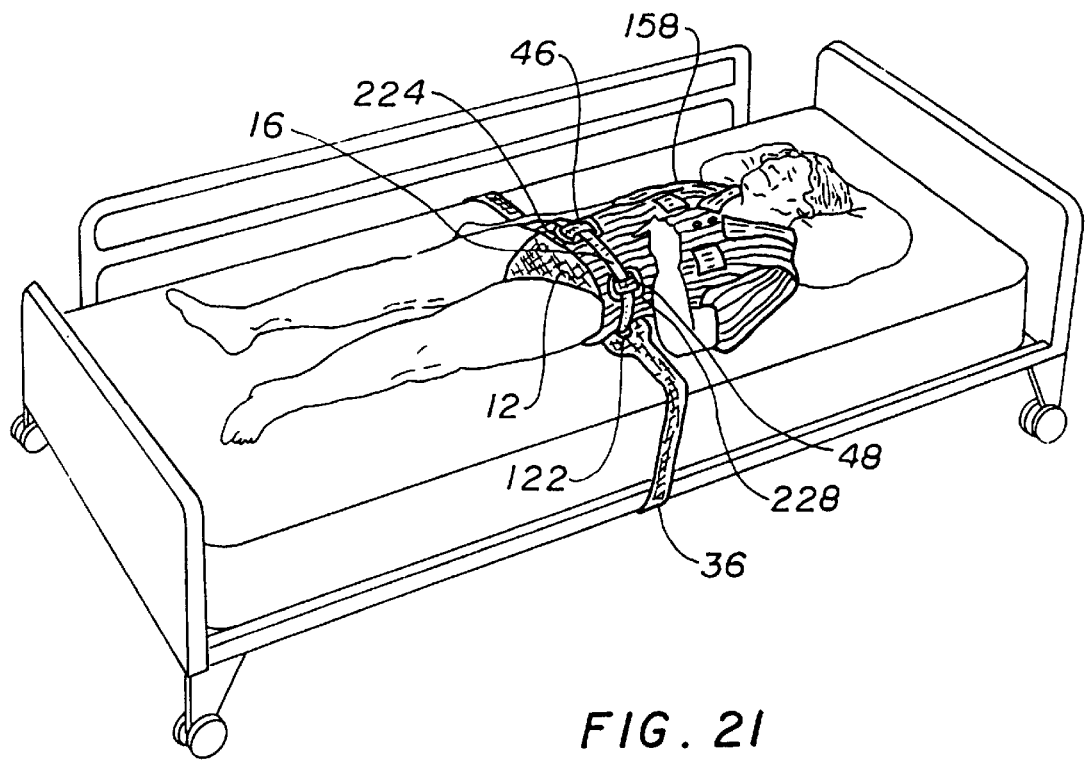
FIG. 21 is a perspective view of the pelvic support and the shirt being used in combination with the bed restraint belt for controlling patient movement in a bed.

FIG. 21 shows another of the multiple applications of the inventive adaptive patient restraint and support system. Pelvic Support 12, Shirt 158, and Bed Restraint Belt 36 are shown controlling the movement of a patient in a bed. Pelvic Support 12 is positioned on the patient. Fastener 38 is connected with Fastener 40 to secure Pelvic Support 12 along the right side of the patient's waist, and Fastener 42 is connected with Fastener 44 to secure Pelvic Support 12 along the left side of the patient's waist. Shirt 158 is positioned on the patient with the waist section of Shirt 158 being positioned over the waist section of Pelvic Support 12. Belt Loop 46 is positioned through Eyelet 224 along the front right waist area of the patient, Belt Loop 48 is positioned through Eyelet 228 along the front left waist area of the patient, and Belt Loop 50 is positioned through Eyelet 232 along the rear center waist area of the patient. The short end of Bed Restraint Belt 36 is positioned around the bed frame on one side of the bed and Fastener 124 is connected with Fastener 126 for interconnecting Bed Restraint Belt 36 with the bed frame. Bed Restraint Belt 36 is positioned horizontally across the bed with Eyelet 122 being positioned in the center of the bed for optimum patient comfort. Bed Restraint Belt 36 is looped around the patient by passing the long end through Belt Loop 46 along the front right waist area of the patient, passing the long end through Belt Loop 48 along the front left waist area of the patient, passing the long end through Belt Loop 50 along the rear center waist area of the patient, and passing the long end through Eyelet 122 behind the patient. The long end of Bed Restraint Belt 36 is positioned around the bed frame on the opposite side of the bed from where the short length of Bed Restraint Belt 36 is attached to the bed frame, and Fastener 128 is connected with Fastener 130 for interconnecting Bed Restraint Belt 36 with the bed frame.

Figure 22:
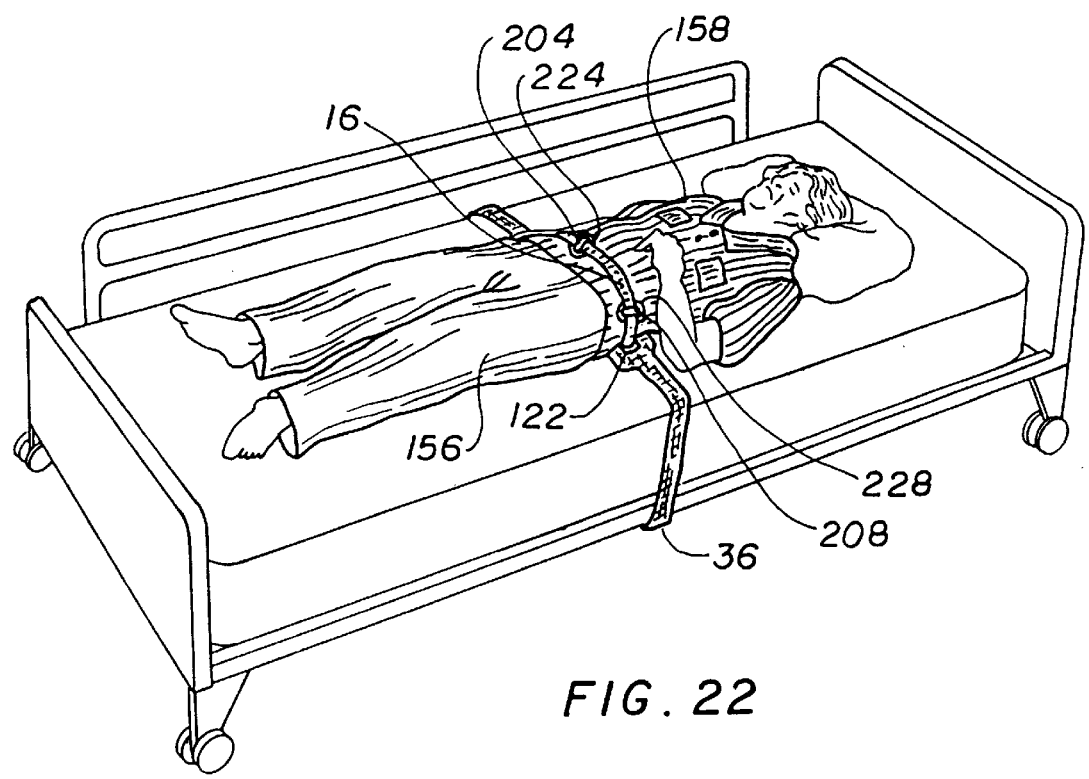
FIG. 22 is a perspective view of the pant and the shirt being used in combination with the bed restraint belt for controlling patient movement in a bed.

FIG. 22 shows another of the multiple applications of the inventive adaptive patient restraint and support system. Pant 156, Shirt 158, and Bed Restraint Belt 36 are shown controlling the movement of a patient in a bed. In a first configuration, Pant 156 and Shirt 158 are positioned on the patient with the waist section of Shirt 158 being positioned over the waist section of Pant 156. Belt Loop 204 is positioned through Eyelet 224 along the front right waist area of the patient, Belt Loop 208 is positioned through Eyelet 228 along the front left waist area of the patient, and Belt Loop 212 is positioned through Eyelet 232 along the rear center waist area of the patient. The short end of Bed Restraint Belt 36 is positioned around the bed frame on one side of the bed and Fastener 124 is connected with Fastener 126 for interconnecting Bed Restraint Belt 36 with the bed frame. Bed Restraint Belt 36 is positioned horizontally across the bed with Eyelet 122 being positioned in the center of the bed for optimum patient comfort. Bed Restraint Belt 36 is looped around the patient by passing the long end through Belt Loop 204 along the front right waist area of the patient, passing the long end through Belt Loop 208 along the front left waist area of the patient, passing the long end through Belt Loop 212 along the rear center waist area of the patient, and passing the long end through Eyelet 122 behind the patient. The long end of Bed Restraint Belt 36 is positioned around the bed frame on the opposite side of the bed from where the short length of Bed Restraint Belt 36 is attached to the bed frame, and Fastener 128 is connected with Fastener 130 for interconnecting Bed Restraint Belt 36 with the bed frame. In a second configuration, Pant 156 and Shirt 158 are positioned on the patient with the waist section of Pant 156 being positioned over the waist section of Shirt 158 (not shown). Belt Loop 222 is positioned through Eyelet 202 along the front right waist area of the patient, Belt Loop 226 is positioned through Eyelet 206 along the front left waist area of the patient, and Belt Loop 230 is positioned through Eyelet 210 along the rear center waist area of the patient. The short end and the long end of Bed Restraint Belt 36 interconnect with the bed the same as in the first configuration. In the second configuration, however, Bed Restraint Belt 36 is looped around the patient by passing the long end through Belt Loop 222 along the front right waist area of the patient, passing the long end through Belt Loop 226 along the front left waist area of the patient, passing the long end through Belt Loop 230 along the rear center waist area of the patient, and passing the long end through Eyelet 122 behind the patient.

Body Suit 152 and Bed Restraint Belt 36 can function to control the movement of a patient in a bed. Body Suit 152 is positioned on the patient with Flap 160 being positioned between the patient's legs and along the front of the patient's waist area. Fastener 176 is connected with Fastener 178 to secure Flap 160 with the front right waist section of Body Suit 152, and Fastener 177 is connected with Fastener 179 to secure Flap 160 with the front left waist section of Body Suit 152. The short end of Bed Restraint Belt 36 is positioned around the bed frame on one side of the bed and Fastener 124 is connected with Fastener 126 for interconnecting Bed Restraint Belt 36 with the bed frame. Bed Restraint Belt 36 is positioned horizontally across the bed with Eyelet 122 being positioned in the center of the bed for optimum patient comfort. Bed Restraint Belt 36 is looped around the patient by passing the long end through Belt Loops 162, 164, 166 along the front waist area of the patient, passing the long end through Belt Loop 174 along the rear center waist area of the patient, and passing the long end through Eyelet 122 behind the patient. The long end of Bed Restraint Belt 36 is positioned around the bed frame on the opposite side of the bed from where the short length of Bed Restraint Belt 36 is attached to the bed frame, and Fastener 128 is connected with Fastener 130 for interconnecting Bed Restraint Belt 36 with the bed frame.

Body Suit 152, Pant 156, and Bed Restraint Belt 36 can function to control the movement of a patient in a bed. Body Suit 152 is positioned on the patient with Flap 160 being positioned between the patient's legs and along the front of the patient's waist area. Fastener 176 is connected with Fastener 178 to secure Flap 160 with the front right waist section of Body Suit 152, and Fastener 177 is connected with Fastener 179 to secure Flap 160 with the front left waist section of Body Suit 152. Pant 156 is positioned on the patient with the waist section of Pant 156 being positioned over the waist section of Body Suit 152. Belt Loop 162 is positioned through Eyelet 202 along the front right waist area of the patient, Belt Loop 164 is positioned through Eyelet 206 along the front left waist area of the patient, and Belt Loop 174 is positioned through Eyelet 210 along the rear center waist area of the patient. The short end of Bed Restraint Belt 36 is positioned around the bed frame on one side of the bed and Fastener 124 is connected with Fastener 126 for interconnecting Bed Restraint Belt 36 with the bed frame. Bed Restraint Belt 36 is positioned horizontally across the bed with Eyelet 122 being positioned in the center of the bed for optimum patient comfort. Bed Restraint Belt 36 is looped around the patient by passing the long end through Belt Loop 162 along the front right waist area of the patient, passing the long end through Belt Loop 164 along the front left waist area of the patient, passing the long end through Belt Loop 174 along the rear center waist area of the patient, and passing the long end through Eyelet 122 behind the patient. The long end of Bed Restraint Belt 36 is positioned around the bed frame on the opposite side of the bed from where the short length of Bed Restraint Belt 36 is attached to the bed frame, and Fastener 128 is connected with Fastener 130 for interconnecting Bed Restraint Belt 36 with the bed frame.

Seating Cushion System 250 functions alone, in combination with Belt System 10, and in combination with Belt System 10 and Garment System 150, for providing supplemental patient support in chair applications, gerichair applications, and wheelchair applications. Seating Cushion System 250 includes Side Support Cushion 252, Side Support Cushion 254, Shoulder Bolster Cushion 256, Shoulder Bolster Cushion 258, Headrest Cushion 260, Back Support Cushion 262, and Wedge Seat Cushion 264. The component cushions of Seating Cushion System 250 are preferred to have a firm inner core made of a foam material surrounded by a removable outer cover made of a washable material.

Side Support Cushions 252, 254 function to provide support to a patient seated in a chair, a gerichair, or a wheelchair. Side Support Cushions 252, 254 are substantially J-shaped to be easily positioned over the arm rests of a chair, a gerichair, or a wheelchair. Side Support Cushions 252, 254 reduce the effective patient seating area so as to provide support along the sides of the patient. Further, Side Support Cushions 252, 254 function as padded arm rests for providing additional patient support.

FIG. 23 and FIG. 24 show another of the multiple applications of the inventive adaptive patient restraint and support system. Side Support Cushions 252, 254 can function concurrently for providing bilateral support on both sides of the seated patient to prevent the patient from leaning to either side. Alternatively, Side Support Cushion 252 or Side Support Cushion 254 can function individually for providing unilateral support on one side of the seated patient to prevent the patient from leaning to that side. Side Support Cushions 252, 254 function alone, in combination with Belt System 10, or in combination with Belt System 10 and Garment System 150, for providing support to a patient seated in a chair, a gerichair, or a wheelchair.

Side Support Cushion 252 can function in combination with Shoulder Bolster Cushion 256, and Side Support Cushion 254 can function in combination with Shoulder Bolster Cushion 258, for providing supplemental support to a patient seated in a chair, a gerichair, or a wheelchair. Side Support Cushion 252 includes Fastener 266 for combining with Shoulder Bolster Cushion 256, and Side Support Cushion 254 includes Fastener 268 for combining with Shoulder Bolster Cushion 258. Shoulder Bolster Cushion 256 includes Fasteners 270 for combining with Side Support Cushion 252, and Shoulder Bolster Cushion 258 includes Fasteners 272 for combining with Side Support Cushion 254. Fastener 270 and Fastener 266 are preferred to be fabricated from a hook-and-loop type material to allow the caregiver to easily position Shoulder Bolster Cushion 256 on Side Support Cushion 252. Fastener 272 and Fastener 268 are preferred to be fabricated from a hook-and-loop type material to allow the caregiver to easily position Shoulder Bolster Cushion 258 on Side Support Cushion 254. Referring to FIG. 23 and FIG. 24, Shoulder Bolster Cushion 256 can be used in combination with Side Support Cushion 252, and Shoulder Bolster Cushion 258 can be used in combination with Side Support Cushion 254, to prevent a patient from slouching in a chair, a gerichair, or a wheelchair. Shoulder Bolster Cushion 256 is attached to Side Support Cushion 252 and Shoulder Bolster Cushion 258 is attached to Side Support Cushion 254 so as to be positioned under the patient's arm pits to provide upper body support to prevent the patient from slouching or slumping in a chair, a gerichair, or a wheelchair. Side Support Cushions 252, 254 and Shoulder Bolster Cushions 256, 258 function alone, in combination with Belt System 10, or in combination with Belt System 10 and Garment System 150, for providing support to a patient seated in a chair, a gerichair, or a wheelchair.

Headrest Cushion 260 functions to stabilize the movement of a patient's head by supporting the patient's head along the front of a chair back or along the front of a gerichair back. Headrest Cushion 260 is configured with Belt Loops 282, 284 on the rear center section of the cushion for receiving Lap Belt 16 therethrough, and with Belt Loop 286 on the rear upper section of the cushion for receiving Chest Belt 20 therethrough.

FIG. 23 and FIG. 24 show another of the multiple applications of the inventive adaptive patient restraint and support system. Headrest Cushion 260 is positioned along the front of the gerichair back at the proper elevation for receiving the patient's head. Lap Belt 16 is first passed through Belt Loops 282, 284, and then passed along on the rear of the gerichair back. Lap Belt 16 is secured by connecting Fastener 64 with Fastener 66. Chest Belt 20 is first passed through Belt Loop 286, and is then positioned over the top of the gerichair back and is then passed around Lap Belt 16 at the rear of the gerichair back. Fastener 72 is connected with Fastener 74 to secure Chest Belt 20. The vertical position of Headrest Cushion 260 relative to a seated patient can be adjusted by shortening or lengthening Chest Belt 20. Headrest Cushion 260 is preferred to be substantially U-shaped to stabilize head movement of a patient requiring assistance in holding his head up. Headrest Cushion 260 functions in combination with Belt System 10, or in combination with Belt System 10 and Garment System 150, for providing supplemental support to a patient seated in a chair or a gerichair.

Back Support Cushion 262 functions to stabilize the movement of a patient's upper body by supporting the patient's back along the front of a chair back, along the front of a gerichair back, or along the front of a wheelchair back. Back Support Cushion 262 is configured with Belt Loops 288, 290 on the rear center section of the cushion for receiving Lap Belt 16 therethrough, and with Belt Loop 292 on the rear upper section of the cushion for receiving Chest Belt 20 therethrough. Back Support Cushion 262 can be used with patient's having kyphosis or certain types of osteoporosis (commonly known as humpback or hunchback).

Figure 26:
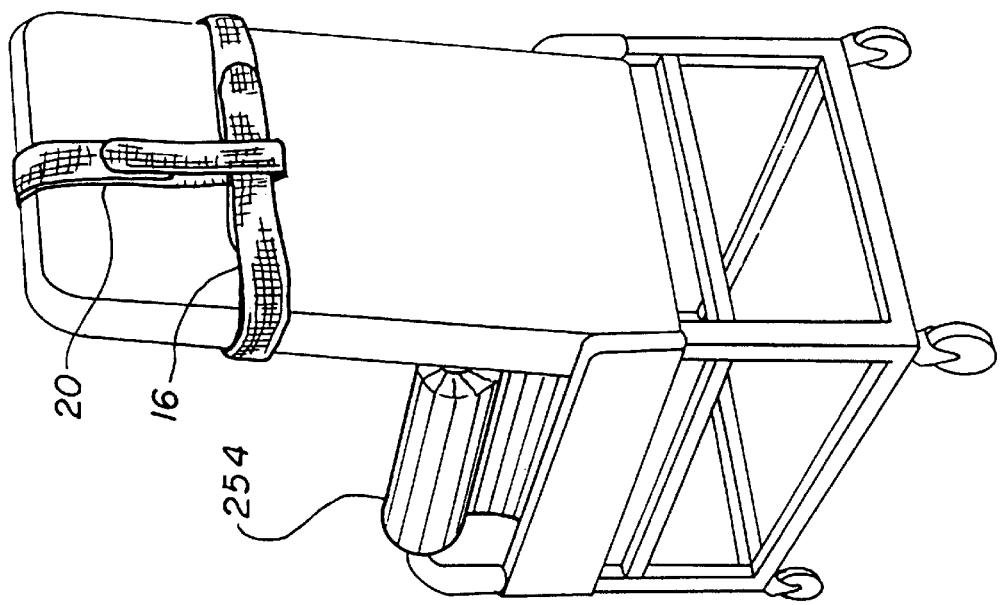
FIG. 26 is a rear side view of the side support cushions, back support cushion, and wedge seat cushion as selectively configured in FIG. 25 being used in combination with the belt system in a gerichair.
Figure 25:
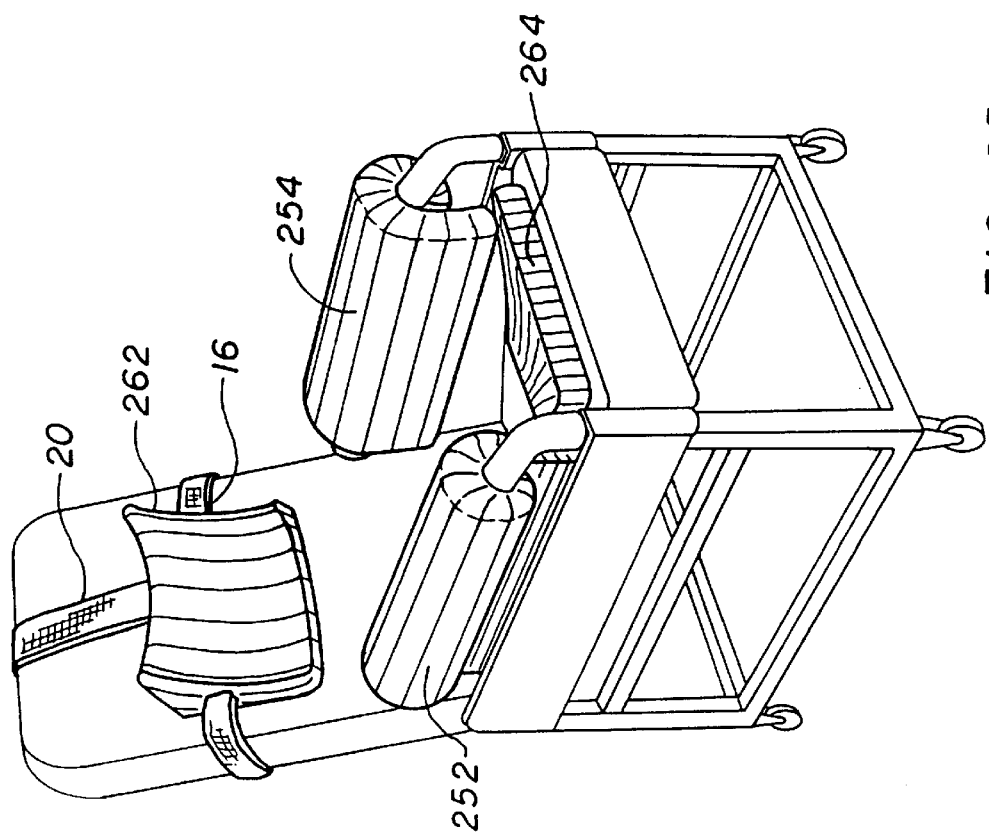
FIG. 25 is a front side view of the side support cushions, back support cushion, and wedge seat cushion being used in combination with the belt system in a gerichair.

FIG. 25 and FIG. 26 show another of the multiple applications of the inventive adaptive patient restraint and support system. Back Support Cushion 262 is positioned on the front of the gerichair back at the proper elevation for receiving the patient's back in a gerichair application. Lap Belt 16 is first passed through Belt Loops 288, 290, and is then passed along the rear of the gerichair back. Lap Belt 16 is secured by connecting Fastener 64 with Fastener 66. Chest Belt 20 is first passed through Belt Loop 292, and is then positioned over the top of the gerichair back and is then passed around Lap Belt 16 along the rear of the gerichair back. Fastener 72 is connected with Fastener 74 to secure Chest Belt 20.

Figure 28:
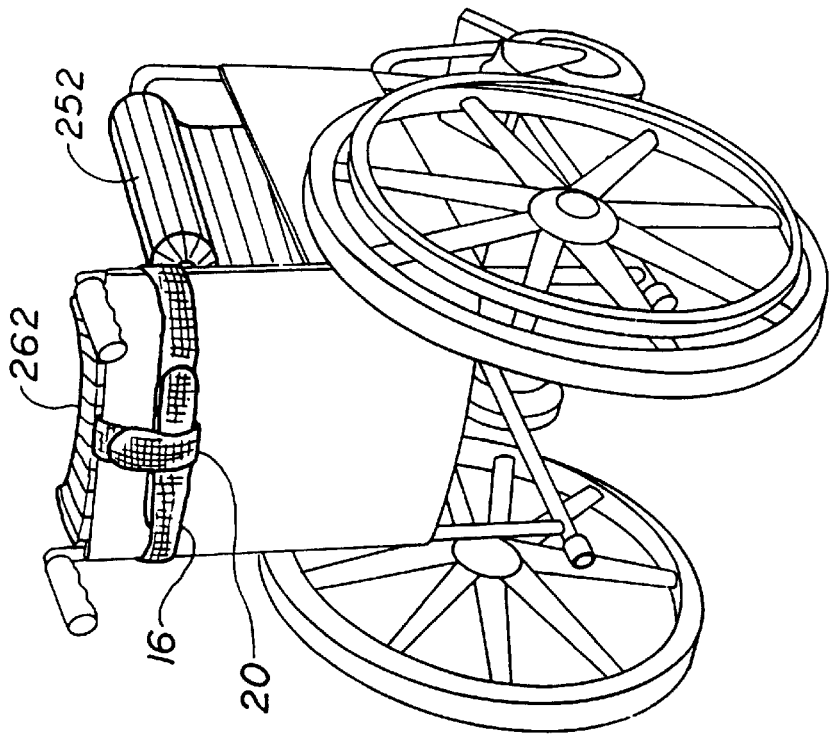
FIG. 28 is a rear view of the side support cushions, back support cushion, and wedge seat cushion as selectively configured in FIG. 27 being used in combination with the belt system in a wheelchair.
Figure 27:
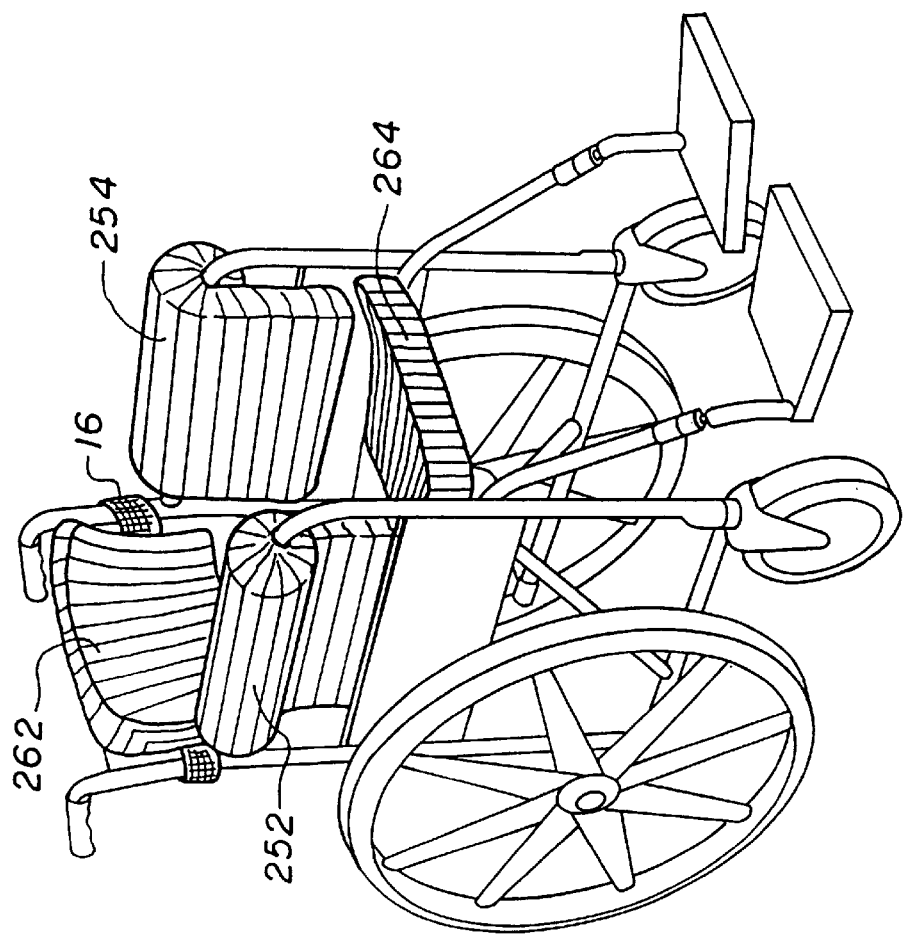
FIG. 27 is a front side view of the side support cushions, back support cushion, and wedge seat cushion being used in combination with the belt system in a wheelchair.

FIG. 27 and FIG. 28 show another of the multiple applications of the inventive adaptive patient restraint and support system. Back Support Cushion 262 is positioned on the front of the wheelchair back at the proper elevation for receiving the patient's back in a wheelchair application. Lap Belt 16 is first passed through Belt Loops 288, 290, and then passed along the rear of the wheelchair back. Lap Belt 16 is secured by connecting Fastener 64 with Fastener 66. Chest Belt 20 is first passed through Belt Loop 292, and is then positioned over the top of the wheelchair back and is then passed around Lap Belt 16 at the rear of the wheelchair back. Fastener 72 is connected with Fastener 74 to secure Chest Belt 20.

In both the gerichair application and the wheelchair application, the vertical position of Back Support Cushion 262 relative to a seated patient can be adjusted by shortening or lengthening Chest Belt 20. Back Support Cushion 262 is shaped to accommodate the curvature of the patient's spine, including curvatures resulting from osteoporosis or kyphosis. Back Support Cushion 262 is preferred to have a non-slip surface on the back side of the cushion to assist in holding the cushion in a relatively fixed position on the front of either the gerichair back or the wheelchair back. Back Support Cushion 260 functions in combination with Belt System 10, or in combination with Belt System 10 and Garment System 150, for providing supplemental support to a patient seated in a chair, a gerichair, or a wheelchair.

Wedge Seat Cushion 264 functions to stabilize the movement of a patient's lower body by supporting the patient's legs along the front of a chair seat, a gerichair seat, or a wheelchair seat.

FIG. 25 and FIG. 26 show another of the multiple applications of the inventive adaptive patient restraint and support system. In a gerichair application, Wedge Seat Cushion 264 is positioned on the top front section of the gerichair seat and functions to elevate a patient's legs to assist in maintaining the patient's lower body in a substantially fixed position against the gerichair back. By maintaining the patient's lower body in a substantially fixed position on the gerichair seat and against the gerichair back, the patient's lower body is supported to assist in preventing the patient from sliding out of the gerichair.

FIG. 27 and FIG. 28 show another of the multiple applications of the inventive adaptive patient restraint and support system. In a wheelchair application, Wedge Seat Cushion 264 is positioned on the top front section of the wheelchair seat and functions to elevate a patient's legs to assist in maintaining the patient's lower body in a substantially fixed position against the wheelchair back in a wheelchair application. By maintaining the patient's lower body in a substantially fixed position on the wheelchair seat and against the wheelchair back, the patient's lower body is supported to assist in preventing the patient from sliding out of the wheelchair. Wedge Seat Cushion 264 is preferred to have a non-skid surface on the bottom to assist in preventing the cushion from sliding. Wedge Seat Cushion 264 functions in combination with Belt System 10, or in combination with Belt System 10 and Garment System 150, for providing supplemental support to a patient seated in a chair, a gerichair, or a wheelchair.

Using Belt System 10, Garment System 150, and Seating Cushion System 250 comprising the present invention, it is an advantage of the present invention to provide adaptive patient support and restraint that can be used to selectively and interchangeably provide physical support, physical restraint, or physical support and physical restraint to a range of patients using various chair sizes and types, various gerichair sizes and types, and various wheelchair sizes and types, and to provide physical restraint to control the movement of a patient in a bed. It is a further advantage of the present invention to provide a patient support and restraint system that permits the patient to maintain an optimum degree of natural freedom of movement so as to minimize the patient's sense of confinement associated with using support and restraint devices. It is a still further advantage of the present invention to comfortably control the patient's movement by using soft, flexible, and stretchable materials that avoid cutting or chafing the patient's skin. It is a still further advantage of the present invention to comfortably control the patient's movement by distributing the support and restraint stresses over a large surface area of the body to minimize causing or contributing to skin disorders. It is a still further advantage of the present invention to provide an adaptive patient support and restraint system that permits the caregiver to adjust the level of physical support or physical restraint to accommodate changes in the patient's health. It is a still further advantage of the present invention to provide a patient support and restraint system that is colorful and fashionable so as to have general consumer appeal. It is a still further advantage of the present invention to provide an integrated patient support and restraint system using modular components to maximize both the system functionality and the system adaptability to complement a comprehensive patient care delivery system. It is a still further advantage of the present invention to provide a low-cost, adaptive patient support and restraint system that is easy for the caregiver to use with a range of patients in a variety of applications. It is a still further advantage of the present invention to permit a moderate range of natural freedom of movement for patient's using the system. It is a still further advantage of the present invention to allow the caregiver to use a single system for interchangeably administering physical support and physical restraint. It is a still further advantage of the present invention to allow the caregiver to gradually decrease the level of support or restraint for a patient whose physical condition improves, and to gradually increase the level of support or restraint for a patient whose physical condition deteriorates.

While the present invention has been illustrated by the description of embodiments thereof, and while the embodiments have been described in considerable detail, it is not the intention of the applicant to restrict or in any way limit the scope of the appended claims to such detail. Additional advantages and modifications will readily appear to those skilled in the art. For example, quick-release type fasteners can be used in place of hook-and-loop type fasteners on belts. In addition, zippers or snaps can be used in place of hook-and-loop type fasteners on garments. Still further, other connector elements can be integrated into the belts, garments, and cushions for interfacing with other patient care delivery systems. In addition, belt loops and eyelets can generally be used interchangeably in Belt System 10, Garment System 150, and Seating Cushion System 250. Therefore, the invention in its broader aspects is not limited to the specific details, representative apparatus, and illustrative examples shown and described. Accordingly, departures may be made from such details without departing from the spirit or scope of the inventors' general inventive concept.

We claim:

1. An adaptive patient support and restraint system for controlling movement of a patient in a chair, said system comprising a pelvic support and one or more differently shaped belts; wherein said system is selectively configurable and interconnectable on the patient and the chair using said pelvic support and said one or more differently shaped belts for controlling movement of the patient by (I) selectably supporting the patient in the chair, (ii) selectably restraining the patient in the chair, or (iii) selectably supporting and selectably restraining the patient in the chair as required by the patient's particular medical or safety needs, and wherein said one or more differently shaped belts includes a pelvic support belt, a lap belt, an anchor belt, a chest belt, a pair of shoulder belts, a pair of torso belts, a lashing belt, and a chair handle belt.

2. An adaptive patient support and restraint system for controlling movement of a patient in a chair, said system comprising:

(a) a pelvic support, said pelvic support including a front lap belt interconnect and a rear pelvic support belt interconnect, and said pelvic support being positioned between the legs and around the waist of the patient;

(b) a pelvic support belt having two ends, said pelvic support belt including a first ring connected to one end and a second ring connected to the other end, said pelvic support belt being interconnected with said rear pelvic support belt interconnect of said pelvic support along the back of the patient, said first ring being positioned along one side of the patient and said second ring being positioned along the other side of the patient; and (c) a lap belt having two ends, said lap belt including a first fastener at one end and a second fastener at the other end;

wherein said lap belt is positioned through said front lap belt interconnect along the front of the patient, through said first ring along one side of the patient, through said second ring along the other side of the patient, and along the rear of the chair back; wherein movement of the patient's body is selectably controllable (i) to support the patient's body by connecting said first fastener with said second fastener within the patient's reach, or (ii) to restrain the patient's body by connecting said first fastener with said second fastener outside of the patient's reach.

3. The adaptive patient support and restraint system of claim 2, said system further comprising an anchor belt having two ends, said anchor belt including a third fastener at one end and a fourth fastener at the other end, said anchor belt being positioned around said lap belt and around a chair member, and wherein said third fastener is connected with said fourth fastener to interconnect said lap belt with the chair member.

4. The adaptive patient support and restraint system of claim 2, said system further comprising a chest belt having two ends, said chest belt including a third fastener at one end and a fourth fastener at the other end, and said chest belt being positioned along the front of the patient's chest, along the sides of the patient's chest, and along the rear of the chair back, wherein movement of the patient's body is selectably controllable (i) to support the patient's body by connecting said third fastener with said fourth fastener within the patient's reach, or (ii) to restrain the patient's body by connecting said third fastener with said fourth fastener outside of the patient's reach.

5. The adaptive patient support and restraint system of claim 4, said system further comprising an anchor belt having two ends, said anchor belt including a fifth fastener at one end and a sixth fastener at the other end, said anchor belt being positioned around said lap belt and around a chair member, and wherein said fifth fastener is connected with said sixth fastener to interconnect said lap belt with the chair member.

6. The adaptive patient support and restraint system of claim 2, said system further comprising:
  (a) a chest belt having two ends, said chest belt including a third fastener at one end and an fourth fastener at the other end;
  (b) a first shoulder belt having two ends, said first shoulder belt including a first chest belt interconnect at one end to interconnect with said chest belt, and a fifth fastener and a sixth fastener at the other end to interconnect with said chest belt, said first shoulder belt being positioned over one of the patient's shoulders; and
  (c) a second shoulder belt having two ends, said second shoulder belt including a second chest belt interconnect at one end to interconnect with said chest belt, and a seventh fastener and an eighth fastener at the other end to interconnect with said chest belt, said second shoulder belt being positioned over the other of the patient's shoulders;
  wherein said chest belt is positioned through said first chest belt interconnect along the front of the patient's chest, through said second chest belt interconnect along the front of the patient's chest, along the sides of the patient, and along the rear of the chair back; wherein said fifth fastener is connected with said sixth fastener to interconnect said first shoulder belt with said chest belt along the rear of the chair back, and said seventh fastener is connected with said eighth fastener to interconnect said second shoulder belt with said chest belt along the rear of the chair back; and
  wherein movement of the patient's body is selectably controllable (i) to support the patient's body by connecting said third fastener with said fourth fastener within the patient's reach, or (ii) to restrain the patient's body by connecting said third fastener with said fourth fastener outside of the patient's reach.

7. The adaptive patient support and restraint system of claim 6, said system further comprising an anchor belt having two ends, said anchor belt including a ninth fastener at one end and a tenth fastener at the other end, said anchor belt being positioned around said lap belt and around a chair member, and wherein said ninth fastener is connected with said tenth fastener to interconnect said lap belt with the chair member.

8. The adaptive patient support and restraint system of claim 6, said system further comprising a lashing belt having two ends, said lashing belt including a ninth fastener at one end and a tenth fastener at the other end, said lashing belt being positioned around said first shoulder belt along the rear of the chair back and around said second shoulder belt along the rear of the chair back, and wherein said ninth fastener is connected with said tenth fastener to interconnect said first shoulder belt with said second shoulder belt.

9. The adaptive patient support and restraint system of claim 2, said system further comprising:
  (a) a chest belt having two ends, said chest belt including a third fastener at one end and a fourth fastener at the other end;
  (b) a first torso belt having two ends, said first torso belt including a fifth fastener and a sixth fastener at one end to interconnect with a first torso belt interconnect of said pelvic support, a first chest belt interconnect adjacent to the one end to interconnect with said chest belt, and a seventh fastener and an eighth fastener at the other end to interconnect with said chest belt, said first torso belt being positioned over one of the patient's shoulders; and
  (c) a second torso belt having two ends, said second torso belt including a ninth fastener and a tenth fastener at one end to interconnect with a second torso belt interconnect of said pelvic support, a second chest belt interconnect adjacent to the one end to interconnect with said chest belt, and an eleventh fastener and a twelfth fastener at the other end to interconnect with said chest belt, said second torso belt being positioned over the other of the patient's shoulders;
  wherein said first torso belt is positioned through said first torso belt interconnect along one front side of the patient and said fifth fastener is connected with said sixth fastener to interconnect said first torso belt with said pelvic support, and said second torso belt is positioned through said second torso belt interconnect along the other front side of the patient and said ninth fastener is connected with said tenth fastener to interconnect said second torso belt with said pelvic support;
  wherein said chest belt is positioned through said first chest belt interconnect along the front of the patient's chest, through said second chest belt interconnect along the front of the patient's chest, along the sides of the patient, and along the rear of the chair back; wherein said seventh fastener is connected with said eighth fastener to interconnect said first torso belt with said chest belt at the rear of the chair back, and said eleventh fastener is connected with said twelfth fastener to interconnect said second torso belt with said chest belt at the rear of the chair back; and
  wherein movement of the patient's body is selectably controllable (i) to support the patient's body by connecting said third fastener with said fourth fastener within the patient's reach, or (ii) to restrain the patient's body by connecting said third fastener with said fourth fastener outside of the patient's reach.

10. The adaptive patient support and restraint system of claim 9, said system further comprising an anchor belt having two ends, said anchor belt including a thirteenth fastener at one end and a fourteenth fastener at the other end, said anchor belt being positioned around said lap belt and around a chair member, and wherein said thirteenth fastener is connected with said fourteenth fastener to interconnect said lap belt with the chair member.

11. The adaptive patient support and restraint system of claim 9, said system further comprising a lashing belt having two ends, said lashing belt including a thirteenth fastener at one end and a fourteenth fastener at the other end, said lashing belt being positioned around said first torso belt along the rear of the chair back and around said second torso belt along the rear of the chair back, and wherein said thirteenth fastener is connected with said fourteenth fastener to interconnect said first torso belt with said second torso belt.

12. An adaptive patient support and restraint system for controlling movement of a patient in a chair by selectably supporting or restraining the patient in the chair, said system comprising:

(a) a pelvic support, said pelvic support including a front lap belt interconnect and a rear lap belt interconnect, and said pelvic support being positioned between the legs of the patient, along the front and sides of the patient's waist, between the chair seat and the chair back, and along the rear of the chair back;

(b) a lap belt having two ends, said lap belt including a first fastener at one end and a second fastener at the other end;

wherein said lap belt is positioned through said front lap belt interconnect support along the front of the patient, along the sides of the patient, and through said rear lap belt interconnect along the rear of the chair back; and wherein movement of the patient's body is selectably controllable (I) to support the patient's body by connecting said first fastener with said second fastener within the patient's reach, or (ii) to restrain the patient's body by connecting said first fastener with said second fastener outside of the patient's reach, and wherein the system further includes:

(c) a chest belt having two ends, said chest belt including a third fastener at one end and a fourth fastener at the other end;

(d) a chair handle belt having two ends for use with a wheelchair, said chair handle belt including a first chair handle interconnect end;

(e) a first shoulder belt having two ends, said first shoulder belt including a first chest belt interconnect at one end to interconnect with said chest belt, and a fifth fastener and a sixth fastener at the other end to interconnect with said chair handle belt, said first shoulder belt being positioned over one of the patient's shoulders; and (f) a second shoulder belt having two ends, said second shoulder belt including a second chest belt interconnect at one end to interconnect with said chest belt, and a seventh fastener and an eighth fastener at the other end to interconnect with said chair handle belt, said second shoulder belt being positioned over the other of the patient's shoulders;

wherein said chair handle belt is positioned on the wheelchair by interconnecting said first chair handle interconnect with a first handle along the rear of the wheelchair and by interconnecting said second chair handle interconnect with a second handle along the rear of the wheelchair;

wherein said chest belt is positioned through said first chest belt interconnect along the front of the patient's chest, through said second chest belt interconnect along the front of the patient's chest, along the sides of the patient, and along the rear of the wheelchair back;

wherein said fifth fastener is connected with said sixth fastener to interconnect said first shoulder belt with said chair handle belt at the rear of the wheelchair, and said seventh fastener is connected with said chair handle belt at the rear of the wheelchair; and wherein movement of the patient's body is selectably controllable (I) to support the patient's body by connecting said third fastener with said fourth fastener within the patient's reach, or (ii) to restrain the patient's body by connecting said third fastener with said fourth fastener outside of the patient's reach.

13. The adaptive patient support and restraint system of claim 12, wherein said chair handle belt further includes an adjuster for changing the length of said chair handle belt to adapt said chair handle belt for use with different size wheelchairs.

14. An adaptive patient support and restraint system for controlling movement of a patient in a chair by selectably supporting or restraining the patient in the chair, said system comprising:

(a) a pelvic support, said pelvic support including a front lap belt interconnect and a rear lap belt interconnect, and said pelvic support being positioned between the legs of the patient, along the front and sides of the patient's waist, between the chair seat and the chair back, and along the rear of the chair back;

(b) a lap belt having two ends, said lap belt including a first fastener at one end and a second fastener at the other end;

wherein said lap belt is positioned through said front lap belt interconnect support along the front of the patient, along the sides of the patient, and through said rear lap belt interconnect along the rear of the chair back; and wherein movement of the patient's body is selectably controllable (I) to support the patient's body by connecting said first fastener with said second fastener within the patient's reach, or (ii) to restrain the patient's body by connecting said first fastener with said second fastener outside of the patient's reach, and wherein the system further includes:

(c) a chest belt having two ends, said chest belt including a third fastener at one end and a fourth fastener at the other end;

(d) a chair handle belt having two ends for use with a wheelchair, said chair handle belt including a first chair handle interconnect at one end and a second chair handle interconnect at the other end;

(e) a first torso belt having two ends, said first torso belt including a fifth fastener and a sixth fastener at one end to interconnect with a first torso belt interconnect of said pelvic support, a first chest belt interconnect adjacent to the one end to interconnect with said chest belt, and a seventh fastener and an eighth fastener at the other end to interconnect with said chair handle belt, said first torso belt being positioned over one of the patient's shoulders; and (f) a second torso belt having two ends, said second torso belt including a ninth fastener and a tenth fastener at one end to interconnect with a second torso belt interconnect of said pelvic support, a second chest belt interconnect adjacent to the one end to interconnect with said chest belt, and an eleventh fastener and a twelfth fastener at the other end to interconnect with said chair handle belt, said second torso belt being positioned over the other of the patient's shoulders; wherein said chair handle belt is positioned on a wheelchair by interconnecting said first chair handle interconnect with a first handle along the rear of the wheelchair and by interconnecting said second chair handle interconnect with a second handle along the rear of the wheelchair, wherein said first torso belt is positioned through said first torso belt interconnect along one front side of the patient and said fifth fastener is connected with said sixth fastener to interconnect said first torso belt with said pelvic support, and said second torso belt is positioned through said second torso belt interconnect along the other front side of the patient and said ninth fastener is connected with said tenth fastener to interconnect said second torso belt with said pelvic support, wherein said chest belt is positioned through said first chest belt interconnect along the front of the patient's chest, through said second chest belt interconnect along the front of the patient's chest, along the sides of the patient, and along the rear of the wheelchair back, wherein said seventh fastener is connected with said eighth fastener to interconnect said first torso belt with said chair handle belt at the rear of the wheelchair, and said eleventh fastener is connected with said twelfth fastener to interconnect said second torso belt with said chair handle belt at the rear of the wheelchair; and wherein movement of the patient's body is selectably controllable (I) to support the patient's body by connecting said third fastener with said fourth fastener within the patient's reach, or (ii) to restrain the patient's upper body by connecting said third fastener with said fourth fastener outside of the patient's reach.

15. The adaptive patient support and restraint system of claim 14, wherein said chair handle belt further includes an adjuster for changing the length of said chair handle belt to adapt said chair handle belt for use with different size wheelchairs.

16. An adaptive patient support and restraint system for controlling movement of a patient in a chair by and for controlling movement of the patient in a bed, said system comprising:

a body suit;
one or more differently shaped belts
a lap robe;
a pant; and
a shirt, and
wherein said body suit includes a plurality of belt loops, said pant includes a plurality of belt loops and a plurality of eyelets, and said shirt includes a plurality of belt loops and a plurality of eyelets, and wherein said body suit, said pant, and said shirt are configurable on the patient, and wherein said body suit, said pant, and said shirt are interconnectable with the chair or the bed using said one or more differently shaped belts and wherein said system is (a) selectively configurable and interconnectable on the patient and the chair, and (b) selectively configurable and interconnectable on the patient and the bed, using said body suit and said one or more belts for controlling movement of the patient by (I) selectably supporting the patient in the chair, (ii) selectably restraining the patient in the chair, (iii) selectably supporting and selectably restraining the patient in the chair, or (iv) restraining the patient in the bed as required by the patient's particular medical and safety needs.

17. An adaptive patient support and restraint system for controlling movement of a patient in a chair, said system comprising:

(a) a body suit, said body suit including a front right lap belt loop, a front center lap belt loop, and a front left lap belt loop, and said body suit being positioned on the upper body and between the legs of the patient; and (b) a lap belt having two ends, said lap belt including a first fastener at one end and a second fastener at the other end; wherein movement of the patient's body is selectably controllable (i) to support the patient's body at the waist by first positioning said lap belt along the rear of the chair back, along the sides of the patient's waist, through said front right lap belt loop along the patient's waist, and through said front left lap belt loop along the patient's waist, and then connecting said first fastener with said second fastener within the patient's reach, or (ii) to restrain the patient's body at the waist by first positioning said lap belt through said front right lap belt loop along the patient's waist, through said front center belt loop along the patient's waist, through said front left lap belt loop along the patients waist, along the sides of the patient, and along the rear of the chair back, and then connecting said first fastener with said second fastener outside of the patient's reach.

18. The adaptive patient support and restraint system of claim 17, said system further comprising a lap robe, said lap robe being positioned around the legs and around the waist of the patient, wherein said lap robe connects to itself at the patient's waist and connects to itself at the patient's knees.

19. The adaptive patient support and restraint system of claim 17, said system further comprising a chest belt having two ends, said chest belt having a third fastener at one end and a fourth fastener at the other end, said chest belt being positioned through a center chest belt loop along the rear of said body suit, and said chest belt being further positioned around the chair back, and wherein said third fastener is connected with said fourth fastener to restrain movement of the patient's upper body.

20. The adaptive patient support and restraint system of claim 17, said system further comprising:

(a) a first chest belt having two ends, said first chest belt having a third fastener at one end and a fourth fastener at the other end; and (b) a second chest belt having two ends, said second chest belt having a fifth fastener at one end and a sixth fastener at the other end;

wherein movement of the patient's upper body is restrained by first positioning said first chest belt through a right chest belt loop along the rear of said shirt, and around said lap belt along the rear of the chair back, and then connecting said third fastener with said fourth fastener; and wherein movement of the patient's body is restrained by first positioning said second chest belt through a left chest belt loop along the rear of said shirt, and around said lap belt along the rear of the chair back, and then connecting said fifth fastener with said sixth fastener.

21. An adaptive patient support and restraint system for controlling movement of a patient in a chair, said system comprising:

(a) a body suit, said body suit including a front right lap belt loop and a front left lap belt loop, and said body suit being positioned on the upper body and between the legs of the patient;

(b) a pant, said pant including a front right eyelet and a front left eyelet, said pant being positioned on the lower body and legs of the patient and over said body suit; and (c) a lap belt having two ends, said lap belt including a first fastener at one end and a second fastener at the other end;

wherein, said front right lap belt loop is positioned through said front right eyelet and said front left lap belt loop is positioned through said front left eyelet; and wherein movement of the patient's body is selectably controllable (i) to support the patient's body at the waist by first positioning said lap belt along the rear of the chair back, along the sides of the patient's waist, through said front right lap belt loop along the patient's waist, and through said front left lap belt loop along the patient's waist, and then connecting said first fastener with said second fastener within the patient's reach, or (ii) to restrain the patient's body at the waist by first positioning said lap belt through said front right lap belt loop along the patient's waist, through said front left lap belt loop along the patients waist, along the sides of the patient, and along the rear of the chair back, and then connecting said first fastener with said second fastener outside of the patient's reach.

22. The adaptive patient support and restraint system of claim 21, said system further comprising a chest belt having two ends, said chest belt having a third fastener at one end and a fourth fastener at the other end, said chest belt being positioned through a center chest belt loop along the rear of said body suit, said chest belt being further positioned around the chair back, and wherein said third fastener is connected with said fourth fastener to restrain movement of the patient's upper body.

23. The adaptive patient support and restraint system of claim 21, said system further comprising:
   (a) a first chest belt having two ends, said first chest belt having a third fastener at one end and a fourth fastener at the other end; and
   (b) a second chest belt having two ends, said second chest belt having a fifth fastener at one end and a sixth fastener at the other end;
   wherein movement of the patient's upper body is restrained by first positioning said first chest belt through a right chest belt loop along the rear of said shirt, and around said lap belt along the rear of the chair back, and then connecting said third fastener with said fourth fastener; and
   wherein movement of the patient's body is restrained by first positioning said second chest belt through a left chest belt loop along the rear of said shirt, and around said lap belt along the rear of the chair back, and then connecting said fifth fastener with said sixth fastener.

24. An adaptive patient support and restraint system for controlling movement of a patient in a chair, said system comprising:
   (a) a pant, said pant including a front right lap belt loop and a front left lap belt loop, and said pant being positioned on the lower body and the legs of the patient;
   (b) a shirt, said shirt including a front right eyelet and a front left eyelet, said shirt being positioned on the upper body of the patient and over said pant; and
   (c) a lap belt having two ends, said lap belt including a first fastener at one end and a second fastener at the other end;
   wherein said front right lap belt loop is positioned through said front right eyelet and said front left lap belt loop is positioned through said front left eyelet; and
   wherein movement of the patient's lower body is selectably controllable (i) to support the patient's body at the waist by first positioning said lap belt along the rear of the chair back, along the sides of the patient's waist, through said front right lap belt loop along the patient's waist, through said front left lap belt loop along the patient's waist, and then connecting said first fastener with said second fastener within the patient's reach, or (ii) to restrain the patient's body at the waist by first positioning said lap belt through said front right lap belt loop along the patient's waist, through said front left lap belt loop along the patients waist, along the sides of the patient, and along the rear of the chair back, and then connecting said first fastener with said second fastener outside of the patient's reach.

25. The adaptive patient support and restraint system of claim 24, said system further comprising a chest belt having two ends, said chest belt having a third fastener at one end and a fourth fastener at the other end, wherein movement of the patient's upper body is restrained by first positioning said chest belt through a center chest belt loop along the rear of said shirt, and around the chair back, and then connecting said third fastener with said fourth fastener.

26. The adaptive patient support and restraint system of claim 24, said system further comprising:
   (a) a first chest belt having two ends, said first chest belt having a third fastener at one end and a fourth fastener at the other end; and
   (b) a second chest belt having two ends, said second chest belt having a fifth fastener at one end and a sixth fastener at the other end;
   wherein movement of the patient's upper body is restrained by first positioning said first chest belt through a right chest belt loop along the rear of said shirt, and around said lap belt along the rear of the chair back, and then connecting said third fastener with said fourth fastener; and
   wherein movement of the patient's body is restrained by first positioning said second chest belt through a left chest belt loop along the rear of said shirt, and around said lap belt along the rear of the chair back, and then connecting said fifth fastener with said sixth fastener.

27. An adaptive patient support and restraint system for controlling movement of a patient in a chair, said system comprising:
   (a) a shirt, said shirt including a front right lap belt loop and a front left lap belt loop, and said shirt being positioned on the upper body of the patient;
   (b) a pant, said pant including a front right eyelet and a front left eyelet, said pant being positioned on the lower body and legs of the patient and over said shirt; and
   (c) a lap belt having two ends, said lap belt including a first fastener at one end and a second fastener at the other end;
   wherein said front right lap belt loop is positioned through said front right eyelet and said front left lap belt loop is positioned through said front left eyelet; and
   wherein movement of the patient's body is selectably controllable (i) to support the patient's body at the waist by first positioning said lap belt along the rear of the chair back, along the sides of the patient's waist, through said front right lap belt loop along the patient's waist, through said front left lap belt loop along the patient's waist, and then connecting said first fastener with said second fastener within the patient's reach, or (ii) to restrain the patient's body at the waist by first positioning said lap belt through said front right lap belt loop along the patient's waist, through said front left lap belt loop along the patients waist, along the sides of the patient, and along the rear of the chair back, and then connecting said first fastener with said second fastener outside of the patient's reach.

28. The adaptive patient support and restraint system of claim 27, said system further comprising a chest belt having two ends, said chest belt having a third fastener at one end and a fourth fastener at the other end, wherein movement of the patient's upper body is restrained by first positioning said chest belt through a center chest belt loop along the rear of said shirt, and around the chair back, and then connecting said third fastener with said fourth fastener.

29. The adaptive patient support and restraint system of claim 27, said system further comprising:
(a) a first chest belt having two ends, said first chest belt having a third fastener at one end and a fourth fastener at the other end; and
(b) a second chest belt having two ends, said second chest belt having a fifth fastener at one end and a sixth fastener at the other end;
wherein movement of the patient's upper body is restrained by first positioning said first chest belt through a right chest belt loop along the rear of said shirt, and around said lap belt along the rear of the chair back, and then connecting said third fastener with said fourth fastener; and
wherein movement of the patient's body is restrained by first positioning said second chest belt through a left chest belt loop along the rear of said shirt, and around said lap belt along the rear of the chair back, and then connecting said fifth fastener with said sixth fastener.

30. An adaptive patient restraint system for controlling movement of a patient in a bed, said system comprising:
(a) a pelvic support, said pelvic support including a front right belt loop, a front left belt loop, and a rear center belt loop, and said pelvic support being positioned around the waist and between the legs of the patient;
(b) a shirt, said shirt including a front right eyelet, a front left eyelet, and a rear center eyelet, and said shirt being positioned on the upper body of the patient and over said pelvic support; and
(c) a bed restraint belt having a long end, a short end, and an aperture therebetween for receiving the long end of said bed restraint belt therethrough, said bed restraint belt including a first fastener and a second fastener at the short end of said belt and a third fastener and a fourth fastener at the long end of said belt;
wherein said front right belt loop is positioned through said front right eyelet, said front left belt loop is positioned through said front left eyelet, and said rear center belt loop is positioned through said rear center eyelet; and
wherein movement of the patient's lower body is restrained by (i) positioning the short end of said belt around a first bed member on one side of the bed and connecting said first fastener with said second fastener to interconnect the short end of said belt with the first bed member, (ii) positioning the long end of said belt through said front right belt loop along the patient's waist, through said front left belt loop along the patient's waist, through said rear center belt loop along the patient's waist, and through said aperture of said belt behind the patient, and (iii) positioning the long end of said belt around a second bed member on the other side of the bed and connecting said third fastener with said fourth fastener to interconnect the long end of said belt with the second bed member.

31. An adaptive patient restraint system for controlling movement of a patient in a bed, said system comprising:
(a) a pant, said pant support including a front right belt loop, a front left belt loop, and a rear center belt loop, and said pant being positioned on the lower body and legs of the patient;
(b) a shirt, said shirt including a front right eyelet, a front left eyelet, and a rear center eyelet, and said shirt being positioned on the upper body of the patient and over said pant along the patient's waist; and
(c) a bed restraint belt having a long end, a short end, and an aperture therebetween for receiving the long end of said bed restraint belt therethrough, said bed restraint belt including a first fastener and a second fastener at the short end of said belt and a third fastener and a fourth fastener at the long end of said belt;
wherein said front right belt loop is positioned through said front right eyelet, said front left belt loop is positioned through said front left eyelet, and said rear center belt loop is positioned through said rear center eyelet; and
wherein movement of the patient's lower body is restrained by (i) positioning the short end of said belt around a first bed member on one side of the bed and connecting said first fastener with said second fastener to interconnect the short end of said belt with the first bed member, (ii) positioning the long end of said belt through said front right belt loop along the patient's waist, through said front left belt loop along the patient's waist, through said rear center belt loop along the patient's waist, and through said aperture of said belt behind the patient, and (iii) positioning the long end of said belt around a second bed member on the other side of the bed and connecting said third fastener with said fourth fastener to interconnect the long end of said belt with the second bed member.

32. An adaptive patient restraint system for controlling movement of a patient in a bed, said system comprising:
(a) a shirt, said shirt including a front right belt, a front left belt loop, and a rear center belt loop, and said shirt being positioned on the upper body of the patient;
(b) a pant, said pant support including a front right eyelet, a front left eyelet, and a rear center eyelet, and said pant being positioned on the lower body and legs of the patient and over said shirt along the patient's waist; and
(c) a bed restraint belt having a long end, a short end, and an aperture therebetween for receiving the long end of said bed restraint belt therethrough, said bed restraint belt including a first fastener and a second fastener at the short end of said belt and a third fastener and a fourth fastener at the long end of said belt;
wherein said front right belt loop is positioned through said front right eyelet, said front left belt loop is positioned through said front left eyelet, and said rear center belt loop is positioned through said rear center eyelet; and
wherein movement of the patient's lower body is restrained by (i) positioning the short end of said belt around a first bed member on one side of the bed and connecting said first fastener with said second fastener to interconnect the short end of said belt with the first bed member, (ii) positioning the long end of said belt through said front right belt loop along the patient's waist, through said front left belt loop along the patient's waist, through said rear center belt loop along the patient's waist, and through said aperture of said belt behind the patient, and (iii) positioning the long end of said belt around a second bed member on the other side of the bed and connecting said third fastener with said fourth fastener to interconnect the long end of said belt with the second bed member.

33. An adaptive patient restraint system for controlling movement of a patient in a bed, said system comprising:

(a) a body suit, said body suit including a front right belt loop, a front left belt loop, and a rear center belt loop, and said body suit being positioned on the upper body and between the legs of the patient;

(b) a pant, said pant including a front right eyelet, a front left eyelet, and a rear center eyelet, and said pant being positioned on the lower body and legs of the patient and over said body suit along the patient's waist; and (c) a bed restraint belt having a long end, a short end, and an aperture therebetween for receiving the long end of said bed restraint belt therethrough, said bed restraint belt including a first fastener and a second fastener at the short end of said belt and a third fastener and a fourth fastener at the long end of said belt;

wherein said front right belt loop is positioned through said front right eyelet, said front left belt loop is positioned through said front left eyelet, and said rear center belt loop is positioned through said rear center eyelet; and wherein movement of the patient's lower body is restrained by (i) positioning the short end of said belt around a first bed member on one side of the bed and connecting said first fastener with said second fastener to interconnect the short end of said belt with the first bed member, (ii) positioning the long end of said belt through said front right belt loop along the patient's waist, through said front left belt loop along the patient's waist, through said rear center belt loop along the patient's waist, and through said aperture of said belt behind the patient, and (iii) positioning the long end of said belt around a second bed member on the other side of the bed and connecting said third fastener with said fourth fastener to interconnect the long end of said belt with the second bed member.

34. An adaptive patient support system for supporting a patient in a chair, said system comprising a first side support cushion, a second side support cushion, a first shoulder bolster cushion, a second shoulder bolster cushion, a headrest cushion, a back support cushion, and a wedge seat cushion, wherein said first side support cushion and said second side support cushion are configurable on the arms of the chair, wherein said first shoulder bolster cushion is configurable on said first side support cushion and said second shoulder bolster cushion is configurable on said second side support cushion, wherein said headrest cushion is configurable on the front of the chair back, said back support cushion is configurable on the front of the chair back, and said wedge seat cushion is configurable on the top of the chair seat, and wherein the component cushions of said system are selectively configurable for selectably supporting the patient in the chair as required by the patient's particular medical or safety needs.

35. An adaptive patient support system for supporting a patient in a chair, said system comprising:

(a) a headrest cushion to support the patient's head, said headrest cushion including a first belt interconnect and a second belt interconnect along the rear of said headrest cushion, and said headrest cushion being shaped to receive the patient's head along the front of said headrest cushion;

(b) a first belt having two ends, said first belt having a first fastener at one end and a second fastener at the other end; and (c) a second belt having two ends, said second belt having a third fastener at one end and a fourth fastener at the other end;

wherein the patient's head is supported by (i) positioning said headrest cushion along the front of the chair back, (ii) interconnecting said headrest cushion with the chair back by first positioning said first belt through said first belt interconnect along the front of the chair back, and around the chair back, and then connecting said first fastener with said second fastener, and (iii) adjusting the vertical position of said headrest cushion by first positioning said second belt through said second belt interconnect along the front of the chair back, over the top of the chair back, and around said first belt along the rear of the chair back, and then connecting said third fastener with said fourth fastener to select the vertical position of said headrest cushion along the front of the chair back.

36. The adaptive patient support system of claim 35, said system further comprising a wedge seat cushion to support the patient's legs, said wedge seat cushion being shaped to receive the patient's legs therein on the top of said wedge seat cushion, wherein the patient's legs are supported by positioning the bottom of said wedge seat cushion on the top of the chair seat.

37. The adaptive patient support system of claim 35, said system further comprising:

(a) a first side support cushion, said first side support cushion being configured to be received by one arm of the chair; and (b) a second side support cushion, said second side support cushion being configured to be received by the other arm of the chair;

wherein said system is selectably configurable (i) to support both sides of the patient in the chair by positioning said first side support cushion on one arm of the chair and positioning said second side support cushion on the other arm of the chair, (ii) to support one side of the patient in the chair by positioning said first side support cushion on one arm of the chair, or (iii) to support the other side of the patient in the chair by positioning said second side support cushion on the other arm of the chair.

38. The adaptive patient support system of claim 37, said system further comprising:

(a) a first shoulder bolster cushion, said first shoulder bolster cushion being configured to be received by said first side support cushion; and (b) a second shoulder bolster cushion, said second shoulder bolster cushion being configured to be received by said second side support cushion;

wherein said system is selectably configurable (i) to support both shoulders of the patient in the chair by positioning said first shoulder bolster cushion on said first side support cushion on one arm of the chair and positioning said second shoulder bolster cushion on said second side support cushion on the other arm of the chair, (ii) to support one shoulder of the patient in the chair by positioning said first shoulder bolster cushion on said first side support cushion on one arm of the chair, or (iii) to support the other shoulder of the patient in the chair by positioning said second shoulder bolster cushion on said second side support cushion on the other arm of the chair.

39. An adaptive patient support system for supporting movement of a patient in a chair, said system comprising:
- (a) a back support cushion to support the patient's back, said back support cushion including a first belt interconnect and a second belt interconnect along the rear of said back support cushion, and said back support cushion being shaped to receive the patient's back along the front of said back support cushion;
- (b) a first belt having two ends, said first belt having a first fastener at one end and a second fastener at the other end; and
- (c) a second belt having two ends, said second belt having third fastener at one end and a fourth fastener at the other end;

wherein the patient's back is supported by (I) positioning said back support cushion along the front of the chair back, (ii) interconnecting said back support cushion with the chair back by first positioning said first belt through said first belt interconnect along the front of the chair back, and around the chair back, and then connecting said first fastener with said second fastener, and (iii) adjusting the vertical position of said back support cushion by first positioning said second belt through said second belt interconnect along the front of the chair back, over the top of the chair back, and around said first belt along the rear of the chair back, and then connecting said third fastener with said fourth fastener to select the vertical position of said back support cushion along the front of the chair back, and wherein the system further includes

- (d) a first shoulder bolster cushion, said first shoulder bolster cushion being configured to be received by said first side support cushion; and
- (e) a second shoulder bolster cushion, said second shoulder bolster cushion being configured to be received by said second side support cushion;

wherein said system is selectably configurable (I) to support both shoulders of the patient in the chair by positioning said first shoulder bolster cushion on said first side support cushion on one arm of the chair and positioning said second shoulder bolster cushion on said second side support cushion on the other arm of the chair, (ii) to support one shoulder of the patient in the chair by positioning said first shoulder bolster cushion on said first side support cushion on one arm of the chair, or (iii) to support the other shoulder of the patient in the chair by positioning said second shoulder bolster cushion on said second side support cushion on the other arm of the chair.

* * * * *